US012226650B2

(12) United States Patent
Karavitis et al.

(10) Patent No.: US 12,226,650 B2
(45) Date of Patent: Feb. 18, 2025

(54) DERMATOLOGICAL LASER SYSTEMS AND METHODS FOR TREATMENT OF TISSUE WITH POOR CHROMOPHORE SELECTIVITY

(71) Applicant: CUTERA, INC., Brisbane, CA (US)

(72) Inventors: Michael A Karavitis, San Pedro, CA (US); Wytze E. van der Veer, Irvine, CA (US); Amogh Kothare, Fremont, CA (US); Soenke A. Moeller, Berkeley, CA (US); Shawn M. Gilliam, Daly City, CA (US); Lukas E. Hunziker, San Jose, CA (US)

(73) Assignee: Cutera, Inc., Brisbane, CA (US)

( * ) Notice: Subject to any disclaimer, the term of this patent is extended or adjusted under 35 U.S.C. 154(b) by 570 days.

(21) Appl. No.: 17/551,152

(22) Filed: Dec. 14, 2021

(65) Prior Publication Data

US 2022/0212027 A1  Jul. 7, 2022

Related U.S. Application Data

(60) Provisional application No. 63/125,377, filed on Dec. 14, 2020.

(51) Int. Cl.
*A61N 5/06* (2006.01)
*A61B 18/00* (2006.01)
*A61N 5/067* (2006.01)

(52) U.S. Cl.
CPC ........... *A61N 5/0616* (2013.01); *A61N 5/067* (2021.08); *A61B 2018/00005* (2013.01);
(Continued)

(58) Field of Classification Search
CPC ................. A61N 5/0616; A61N 5/067; A61N 2005/0651; A61N 2005/066;
(Continued)

(56) References Cited

U.S. PATENT DOCUMENTS 7,245,369 B2   7/2007  Wang et al.
2008/0080585 A1   4/2008  Glebov et al.
(Continued)

FOREIGN PATENT DOCUMENTS

EP   1579539 B1   3/2008

OTHER PUBLICATIONS

Thompson, Daniel J. et al., "Narrow Linewidth Tunable External Cavity Diode Laser Using Wide Bandwith Filter," AIP, Review of Scientific Instruments, 83, 023107, Feb. 24, 2012, Australia, 6 pages.
(Continued)

*Primary Examiner* — Michael J Lau
*Assistant Examiner* — Anh-Khoa N Dinh
(74) *Attorney, Agent, or Firm* — McCarter & English, LLP

(57) ABSTRACT

Dermatological systems and methods for providing a therapeutic laser treatment of tissue having poor chromophore selectivity using a laser source having a grating element to provide laser light having reduced linewidth. In some embodiments, the linewidth is reduced by at least half compared to the linewidth that would be provided in a system without the grating filter element. The linewidth may be reduced in some cases to 500 GHz or less, 300 GHz or less, or 200 Hz or less.

29 Claims, 17 Drawing Sheets

(52) U.S. Cl.
CPC ........... *A61B 2018/00714* (2013.01); *A61B 2018/00732* (2013.01); *A61N 2005/0651* (2013.01); *A61N 2005/066* (2013.01); *A61N 2005/0667* (2013.01)

(58) Field of Classification Search
CPC ...... A61N 2005/0667; A61N 2005/063; A61N 2005/0647; A61N 2005/0659; A61N 5/0613; A61N 5/0622; A61N 2005/0644; A61N 5/0624; A61N 5/0625; A61B 2018/00005; A61B 2018/00714; A61B 2018/00732; A61B 18/203; A61B 2018/00047; A61B 2018/00452; A61B 2018/00642; A61B 2018/00648; A61B 2018/0066; A61B 2018/00678; A61B 2018/00708; A61B 2018/00785; A61B 2018/00809; A61B 2090/065; H01S 5/0014; H01S 5/12; H01S 5/125; H01S 5/141
See application file for complete search history.

(56) References Cited

U.S. PATENT DOCUMENTS

2011/0060266 A1\* 3/2011 Streeter ............... A61N 5/0613
604/20
2017/0063468 A1 3/2017 Guo et al.

OTHER PUBLICATIONS

Ricci, L. et al., "A Compact Grating-Stabilized Diode Laser System For Atomic Physics," Optics Communications, 117, Germany, Jun. 15, 1995, pp. 541-549.
Wenzel, H. et al., "Design and Realization of High-Power DFB Lasers," Proceedings of SPIE, vol. 5594, Optics East, 2004, US, 15 pages.
Vaissie, Laurent, "Bright Laser Diodes Combat Cancer," BioOptics World, Jul./Aug. 2009, US, 4 pages.

\* cited by examiner

1220 ⤴

1222 — Using a laser system that includes a laser gain medium that in the absence of a grating filter element, would produce laser light having a center frequency within the first frequency range and a first frequency linewidth of at least 1000 GHz

1224 — Using a laser system that includes a grating filter element that can provide feedback to the light in the laser gain medium, and wherein the grating element is capable of reducing the 1$^{st}$ frequency linewidth to a 2$^{nd}$ frequency linewidth that is no more than ½ of the 1$^{st}$ frequency linewidth

1226 — Using a laser system that includes an output coupling capable of providing a predetermined fraction of light from the laser gain medium To Block 1230 of Fig. 12A

FIG. 12C

DERMATOLOGICAL LASER SYSTEMS AND METHODS FOR TREATMENT OF TISSUE WITH POOR CHROMOPHORE SELECTIVITY

CROSS-REFERENCE TO RELATED APPLICATIONS

This application claims the benefit of priority of U.S. Provisional Application Ser. No. 63/125,377, filed Dec. 14, 2020, entitled "Dermatological Laser Systems and Methods for Treatment of Tissue With Poor Chromophore Selectivity," which is hereby incorporated by reference herein in its entirety. This application is related to U.S. patent application Ser. No. 17/120,237, filed Dec. 13, 2020, entitled "Dermatological Systems and Methods With Handpiece for Coaxial Pulse Delivery and Temperature Sensing," which is a continuation-in-part of U.S. patent application Ser. No. 16/805,761, filed Feb. 29, 2020, now U.S. Pat. No. 10,864,380 B1, entitled "Systems and Methods for Controlling Therapeutic Laser Pulse Duration," which is also related to the present application. Both applications are hereby incorporated by reference herein in their entirety. This application is also related to U.S. Provisional Application Ser. No. 63/125,354, filed Dec. 14, 2020, entitled "Dermatological Laser Systems and Methods with Pressure Sensing Handpiece," which is hereby incorporated by reference herein in its entirety.

BACKGROUND OF THE INVENTION

This invention relates generally to laser-based medical treatment systems, and more specifically to the treatment of dermatological conditions in tissues having poor chromophore selectivity using wavelength-stabilized laser light.

A variety of dermatological conditions are treatable using electromagnetic radiation (EMR), including specifically laser, to treat a range of conditions including acne vulgaris, abnormal pigmentation, vascular skin conditions (e.g., spider veins), wrinkles and fine lines, dyschromia, and many others. Both pulsed and continuous-wave (CW) laser systems have been used.

Many such systems use a laser to photo-thermally damage a target tissue while preserving surrounding or adjacent non-targeted tissues or structures. The principle of selective photothermolysis, which involves thermally damaging a target tissue to promote a healing response, has led to the development of a variety of laser applications as standard of care in many medical fields including dermatology.

Damaging tissue by photothermolysis involves raising the temperature of the target tissue to a damage threshold temperature for a specified time period. For a desired level of thermal damage, there is a tradeoff between the temperature the target tissue must reach and the time that the temperature must be maintained. The same thermal damage may be achieved using a lower temperature by increasing the time of heating, or using a higher temperature with shorter heating time. To avoid thermal damage to non-targeted tissue, it is desirable to limit the heating time to the thermal relaxation time (TRT) of the target tissue, which is the time required for the target to dissipate about 63% of the thermal energy received from the laser pulse. TRT is related to the size of the target chromophore, and may range from a few nanoseconds for small chromophores such as tattoo ink particles, to hundreds of milliseconds for large chromophores such as leg venules. The TRT for a target tissue may be used for a particular laser system to select appropriate damage threshold temperatures for a desired level of thermal damage. Depending upon factors such as the laser power, fluence, spot size, etc. used in a given system, a damage threshold temperature to achieve a desired level of photothermolysis at time periods approximately equal to the TRT may be selected, minimizing damage to non-target tissues.

Photothermolysis can be achieved when three conditions are met: 1) the wavelength of the laser is chosen to have a preferential absorption in the target tissue over non-target tissue; 2) the laser pulse duration should be equal to or less than (=<) the TRT of the target tissue; and 3) the laser fluence (i.e., energy per unit area) must be sufficient to exceed the thermal damage threshold of the target tissue. Together, these principles permit laser systems to be developed that deliver energy at specific wavelengths, pulse durations, and fluences to provide controlled energy to damage target tissue while leaving non-targeted surrounding tissues and structures substantially unaffected.

Ideally, thermal damage is highly localized to only the particular target tissue (e.g., particular structures such as chromophores within a skin layer at a particular location, with nearby non-targeted tissues/structures remaining unaffected and available to facilitate the healing response in the targeted tissue. However, the structural complexity of the skin, which includes a variety of layers each having unique structural and functional characteristics, has limited the development of effective laser treatments for many skin conditions.

Effectively reaching and limiting thermal damage to target structures within skin tissue by laser radiation is complicated by a variety of intrinsic and extrinsic factors. Intrinsic factors include, without limitation, the depth of the target structure within tissue and the associated absorption of light by non-targeted structures overlying the target (which may involve a plurality of intervening structures each having different light absorption and thermal characteristics), the scattering of light within the skin above the target, the TRT of the target structure and intervening non-target structures, and the removal (or non-removal) of heat by blood flowing through dermal and subdermal layers. Extrinsic factors include, also without limitation, the wavelength, pulse width, power, fluence, spot size, and other characteristics of the laser used to treat the target tissue or structure.

Where a chromophore present in a target tissue has a highly preferential absorption at a particular wavelength compared to other chromophores in the region of the target tissue, non-targeted tissue, it is possible to selectively damage the target tissue by applying laser light at the highly absorbed wavelength, which selectively causes thermal damage to the target tissue while having relatively little effect on non-target tissues. However, in many instances, chromophores in the target tissue have similar absorption coefficients as non-target chromophores over a wide range of wavelengths. The relative absorption of two chromophores at a particular wavelength can be expressed as the ratio of the absorption coefficients. Where the ratio of a target chromophore to a non-target chromophore is ten (10) or greater for a particular wavelength (or wavelength range), if a laser at the wavelength or within the wavelength range can be provided, relatively good selectivity between the non-target and target chromophores can be achieved. Where the absorption coefficient ratio is less than ten, however, both the target and non-target chromophores will absorb significant amounts of the laser light, and consequently thermal damage to non-target tissues is likely. In addition, in many instances the ratios of the chromophores change over a relatively short wavelength range, and the absorption coefficient of the target chromophore only exceeds the absorption coefficient of the non-target chromophore for a relatively narrow wavelength range. Under these conditions, unless a laser having a precise wavelength is available, selectivity is again poor.

For tissues in which the ratio of a target chromophore in a target tissue to a non-target chromophore in a non-target tissue exceeds ten (10) over a wavelength range of 10000 GHz or greater, relatively good selectivity between heating target and non-target chromophores can be achieved. Where either the target/non-target chromophore absorption coefficient ratio is less than ten, or the ratio falls below ten over a relatively short wavelength range, the target tissue has poor chromophore selectivity. In some cases, the absorption coefficient of the target chromophore only exceeds the absorption coefficient of the non-target chromophore over a relatively narrow wavelength range. Where the ratio is both less than ten and changes rapidly over a short wavelength range, the non-target tissue may experience significant thermal damage along with the target tissue. As used herein, the term "poor chromophore selectivity" refers to a target tissues for which 1) the absorption coefficient of a target chromophore exceeds the absorption coefficient of one or more non-target chromophores over a first frequency range of less than 6000 GHz, and 2) the maximum value of the ratio of the absorption coefficient of the target and non-target chromophores is less than ten (10) throughout the first frequency range.

[0011] The range of wavelengths of light output by a laser source is referred to as the laser "linewidth." Commercially available diode lasers having a narrow linewidth are photo thermolysis available for a limited number of crystals that lase at specific wavelengths (e.g., Nd:YAG lasers, Er:YAG lasers). Diode lasers can be designed to lase at specified wavelengths, but diode lasers generally have relatively wide linewidths. Diode lasers with relatively narrow linewidths are generally available only at high financial or system complexity costs. Currently available commercial diode lasers for dermatological systems typically have linewidths of 1000 GHz or greater. In other applications such as for the treatment of vascular conditions, frequency doubled Nd:YAG lasers provide the narrow linewidth at the needed center frequency. Solid-state lasers are typically the preferred solution where available, as they can achieve higher peak powers and are typically less costly to build.

One example of a semiconductor diode laser is a Fabry-Perot laser, which has an active medium and broad-band reflectors at each end. Due to the effect of stimulated emission, the probability to emit a photon with a specific direction and wavelength increases proportionally to the number of photons of the same characteristics already present in the laser medium. Accordingly, the laser emits light at a wavelength that is given by the longitudinal modes formed by the distance of the two mirrors. Because of the broadband nature of the mirrors and the broad gain region of typical semiconductor materials, a multitude of longitudinal modes is supported, resulting in a relatively wide linewidth. The wavelengths that are amplified by the gain medium are temperature dependent, as is the refractive index, and as such the output wavelength of the laser and as a result the output wavelength is unstable and highly temperature dependent.

Acne vulgaris, more commonly referred to simply as acne, is the most common reason for office visits to dermatologists in the United States. Over 60 million Americans suffer from acne. Treatment options include topical applications such as disinfectants (e.g., benzoyl peroxide), retinoids (e.g., Retin-A), and antibiotics (e.g., clindamycin and erythromycin), as well as ingested compounds such as antibiotics (e.g., tetracycline), hormonal treatments (e.g., birth control pills), isotretinoin (Accutane, which has significant side effects), and optical treatments such as lasers. Laser treatments have the benefit of avoiding the side effects and inconvenience of pharmaceuticals and topical treatments but, at present, have limited effectiveness for reasons including the previously noted complexity of skin tissue structures and limitations of existing laser systems. More recently, nanosphere particles have been deposited into skin pores and/or follicles, followed by heating of the nanoparticles with laser light to treat acne. Photodynamic therapies, in which an agent is applied to the skin to increase its sensitivity to light, have also been used in conjunction with laser or other light (e.g., blue light) to treat acne.

There is a need for improved laser systems having greater efficacy for treating acne. The present invention discloses systems and methods for laser treatment of tissues having poor chromophore selectivity using laser sources providing reduced laser linewidth to provide improved selectivity of a target chromophore. Acne involves clogged oil pores of the sebaceous glands, which are located in the dermis and present a deep target with a high risk of thermally damaging overlying tissue when treated with laser light. Moreover, in many cases the absorption coefficient for oil is less than that of the major competing chromophore, i.e., water. Even in the relatively narrow laser wavelength ranges (e.g., about 1690-1740 nm) where the absorption coefficient of oil/sebum exceeds that of water, it does so by only a factor of about 2, i.e., the sebaceous gland has poor chromophore selectivity.

In one aspect, the present disclosure provides laser systems laser sources producing laser light having a reduced linewidth and an output wavelength that is selectively absorbed by a target chromophore. In some embodiments, the systems include a handpiece for applying the laser light to a target tissue having poor chromophore selectivity, with a contact cooling element to cool the target tissue and a temperature determination unit for determining the temperature of the target tissue receiving the laser pulses. Systems of the present invention provide improved skin temperature control during the treatment of tissue with poor chromophore selectivity to avoid damage to non-target structures and/or chromophores, more precisely control thermal damage to target structures, and promote a more thorough and rapid healing response. In one aspect, the disclosure provides systems and methods having a laser source having a grating filter element and a handpiece to cool and deliver laser pulses to a target skin area. A grating filter element is an optical element that reflects incident light at an angle that is dependent on the wavelength. As such, a grating can split a polychromatic beam into its components similar to a prism. A Bragg grating is a transparent device with a periodic variation of the refractive index. It reflects light as long as the Bragg condition is fulfilled. As the reflection is wavelength-dependent, it can act as a wavelength selective device. Substituted for one of the mirrors in a Fabry-Perot laser, its wavelength selectivity can be used in embodiments of the present invention as part of a laser treatment system providing improved treatment for tissues having poor chromophore selectivity. In one embodiment, the handpiece includes optical elements to direct laser pulses to the target tissue along a first optical path, and a contact cooling unit to cool the surface of a target skin area receiving laser light. In one embodiment, the handpiece further includes a temperature determination unit to determine the surface temperature of a target skin area using infrared (IR) energy radiated from substantially only the target skin areas along a second optical path that is substantially counterdirectional to the first optical path along which the laser pulses are delivered. The surface temperature may be determined before, during, or after the delivery of the laser pulses. In one embodiment, the temperature of a target temperature area is determined a plurality of times before and during the delivery of a laser pulse. In preferred embodiments, the first and second optical paths have a common optical axis for at least a portion of each optical path.

Precise temperature control of the target skin area becomes highly important when the patient's skin varies in thickness or composition, such that target skin areas (e.g., spots to which one or more laser pulses are applied) may reach significantly different temperatures when the same laser pulse is applied to different skin areas. The disparity in skin temperatures for a pre-defined laser pulse for different skin areas is magnified when a target structure (e.g., a sebaceous gland or sebum) is deeper in the skin, because of the greater scattering and absorption of energy by overlying tissue that occurs before the light reaches the deeper target structure.

Heating in tissues depends upon both the absorption coefficient of the irradiated tissue structures for the wavelength of laser light used, as well as thermal relaxation times, which is a measure of how rapidly the affected structure returns to its original temperature. By delivering the laser energy in a pulse with a time duration less than the TRT of the target, highly localized heating (and destruction) of a tissue target structure (e.g., melanin, sebum, sebaceous gland, collagen) can be achieved, minimizing damage to non-target structures (e.g., non-targeted skin layers, blood vessels, etc.). If the laser pulse duration is less than the TRT of the target tissue, no significant heat can escape into non-target structures, and damage to non-target structures is limited.

For deeper target structures such as sebaceous glands, which often range from 0.3-2.0 mm (more commonly 0.5-1.0 mm) below the outer surface of the epidermis, damage to overlying tissue structures is difficult to control or limit, since the laser energy must pass through those tissue structures before reaching the target tissue structures. The overlying tissue structures absorb energy depending upon their respective depths and absorption coefficients, and undesired damage may frequently occur. In some instances, the target structures are either sufficiently shallow, or the treatment temperature to which the target structures are raised is sufficiently low, that the heating of overlying structures may not cause excessive damage. Even where the risk of overheating the overlying structures of a relatively deep target is minimal, however, accurate temperature control of the target structure may be poor, resulting in overheating or underheating or the target structure, discomfort to the patient, or a combination of such undesired effects.

The skin surface may be cooled to limit the temperature increase (and damage) to non-target overlying structures, and to limit patient discomfort or pain. However, existing systems lack precise control of the cooling process. Achieving both a desired level of photothermal damage to deeper target structures and minimizing damage to non-target overlying structures has proven elusive. In many cases, the skin is cooled either too much—in which case the deeper target structure fails to reach a temperature damage threshold—or too little, in which case non-target overlying structures are damaged and the deeper target structure may be excessively damaged. There is a need for laser-based treatment systems having improved temperature control of the cooling process to ensure that target structures reach a desired temperature (e.g., a thermal damage temperature) and that thermal damage to non-target structures is minimized or controlled to an acceptable level. There is a need for dermatological laser systems that are able to efficiently treat a variety of medical conditions to achieve these goals.

SUMMARY

In one embodiment, the invention comprises a method of treating a target tissue having poor chromophore selectivity relative to a non-target tissue, the method comprising: a) selecting for treatment a target tissue comprising a first tissue structure comprising a target chromophore and a second tissue structure comprising at least one non-target chromophore, wherein the absorption coefficient of the target chromophore continuously exceeds the absorption coefficient of the at least one non-target chromophore over a first frequency range of less than 6000 GHz, and the maximum value of the ratio of the absorption coefficient of the target chromophore to the absorption coefficient of the non-target chromophore over the first frequency range is less than 10; b) providing a diode laser system comprising at least one semiconductor laser comprising: 1) a semiconductor laser gain medium that, in the absence of a grating filter element, is adapted to produce laser light having a center frequency within the first frequency range and a first frequency linewidth of at least 1000 GHz; 2) a grating filter element capable of providing feedback to the light produced in the laser gain medium, wherein the grating element is further capable of reducing the first frequency linewidth to a second frequency linewidth that is no more than one-half of the first frequency linewidth; and 3) an output coupling adapted to output a desired fraction of light from the semiconductor laser gain medium; c) generating laser light having the first frequency linewidth in the resonant cavity; d) filtering the generated laser light using the grating filter element; e) outputting from the output coupling laser light having the center frequency and a second frequency linewidth of no more than 500 GHz; and f) applying the laser light output from the output coupling to the target tissue to selectively heat the target chromophore relative to the non-target chromophore. In one embodiment, outputting laser light from the output coupler comprises outputting laser light having the center frequency and a second frequency linewidth of no more than 300 GHz. In one embodiment, wherein the grating filter element is adapted to reduce the first frequency linewidth by at least 75%.

In one embodiment, the invention comprises a method of treating a target tissue having poor chromophore selectivity relative to a non-target tissue, the method comprising: a) selecting for treatment a target tissue comprising a first tissue structure comprising a target chromophore and a second tissue structure comprising at least one non-target chromophore, wherein the absorption coefficient of the target chromophore continuously exceeds the absorption coefficient of the at least one non-target chromophore over a first frequency range of less than 6000 GHz, and the maximum value of the ratio of the absorption coefficient of the target chromophore to the absorption coefficient of the non-target chromophore over the first frequency range is less than 10; b) providing a diode laser system comprising at least one semiconductor laser comprising: 1) a semiconductor laser gain medium that, in the absence of a grating filter element, is adapted to produce laser light having a center frequency within the first frequency range and a first frequency linewidth of at least 1000 GHz; 2) a grating filter element capable of providing feedback to the light produced in the laser gain medium, wherein the grating element is further capable of reducing the first frequency linewidth to a second frequency linewidth that is no more than one-half of the first frequency linewidth; and 3) an output coupling adapted to output a desired fraction of light from the semiconductor laser gain medium; c) generating laser light having the first frequency linewidth in the resonant cavity; d) filtering the generated laser light using the grating filter element; e) outputting from the output coupling laser light having the center frequency and a second frequency linewidth of no more than 500 GHz; and f) applying the laser light output from the output coupling to the target tissue to selectively heat the target chromophore relative to the non-target chromophore. In one embodiment, outputting laser light from the output coupler comprises outputting laser light having the center frequency and a second frequency linewidth of no more than 300 GHz. In one embodiment, wherein the grating filter element is adapted to reduce the first frequency linewidth by at least 75%.

In one embodiment, the invention comprises a method of selectively treating sebum in a target tissue comprising sebum and water as chromophores, comprising: a) selecting a skin area comprising a sebaceous gland as a target chromophore and water as a non-target chromophore for treatment with one or more therapeutic laser pulses with laser light having a wavelength within a first frequency range of about 1690-1740 nm, wherein the maximum value of the ratio of the absorption coefficient of sebum to the absorption coefficient of water over the first frequency range is less than 5; b) providing a diode laser system comprising at least one semiconductor laser comprising: 1) a semiconductor laser gain medium that, in the absence of a grating filter element, is adapted to produce laser light having a center frequency within the first frequency range and a first frequency linewidth of at least 1000 GHz; 2) a grating filter element capable of providing feedback to the laser light produced in the laser gain medium, wherein the grating element is further capable of reducing the first frequency linewidth to a second frequency linewidth that is no more than one-half of the first frequency linewidth; and 3) an output coupling adapted to output a desired fraction of light from the semiconductor laser gain medium; c) generating laser light having the first frequency linewidth in the resonant cavity; d) filtering the generated laser light using the grating filter element; e) outputting from the output coupling laser light having the center frequency and a second frequency linewidth of no more than 300 GHz; and f) applying the laser light output from the output coupling to the target tissue to selectively heat the sebum relative to water in the target tissue.

In one embodiment, the invention comprises a system for treating a target tissue having poor chromophore selectivity, the target tissue comprising a first tissue structure comprising a target chromophore and a second tissue structure comprising a non-target chromophore, wherein the absorption coefficient of the target chromophore continuously exceeds the absorption coefficient of the at least one non-target chromophore over a first frequency range of less than 6000 GHz, and the maximum value of the ratio of the absorption coefficient of the target chromophore to the absorption coefficient of the non-target chromophore over the first frequency range is less than 10, the system comprising: a) a diode laser system having at least one semiconductor laser generating pulsed laser light, the at least one semiconductor laser comprising: 1) a semiconductor laser gain medium that, in the absence of a grating filter element, produces laser light having a center frequency within the first frequency range and a first frequency linewidth of at least 1000 GHz; 2) a grating filter element capable of providing feedback to the light in the laser gain medium, wherein the grating element is adapted to reduce the first frequency linewidth to a second frequency linewidth that is no more than one-half of the first frequency linewidth; and 3) an output coupling adapted to output a desired fraction of light from the semiconductor laser gain medium as laser pulses; b) a handpiece to receive the laser pulses output from the diode laser system and to direct the laser pulses to the target tissue along a first optical path. In one embodiment, the handpiece comprises: 1) an optical connector to receive the laser light output from the output coupling of the diode laser system; 2) a contact cooling element comprising a cooling window adapted to contact and cool a first skin area of the patient, wherein the cooling window comprises a thermally conductive material and wherein the target tissue comprises a volume of tissue having an external skin surface within the first skin area; and 3) at least one optical element located in the first optical path and adapted to direct the laser light along the first optical path from the optical connector through the cooling window into the target tissue, and the system further comprises a temperature determination unit that determines a surface temperature of the target tissue one or more times before, during, or after the application of each laser pulse.

BRIEF DESCRIPTION OF THE DRAWINGS

FIG. 12C is a flowchart depiction of a more detailed description for providing a semiconductor laser or diode laser system, in accordance with an embodiment herein.

DESCRIPTION

Figure 1:
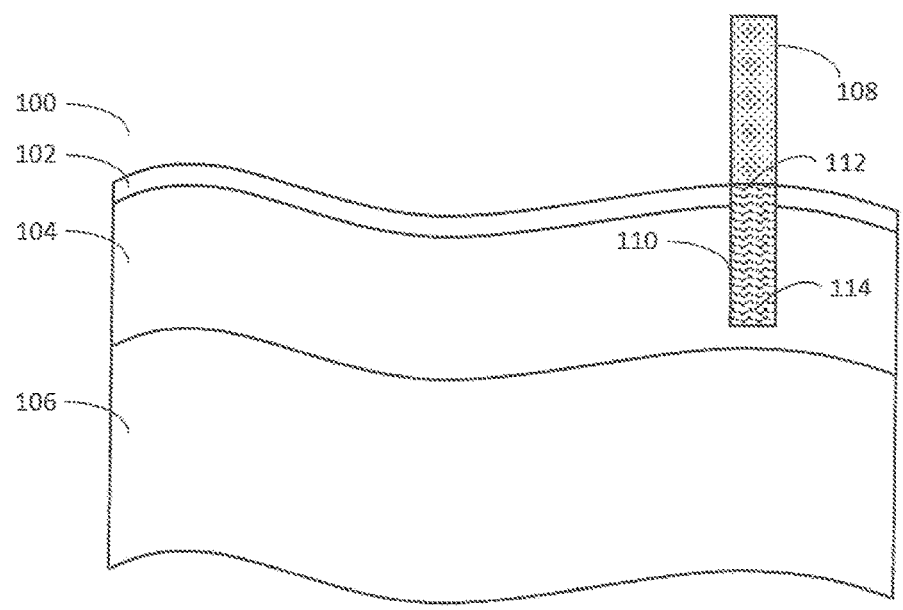
FIG. 1 is a cross-sectional illustration of skin tissue depicting the epidermis, dermis, and hypodermis, with a laser pulse applied to a portion thereof.

Exemplary embodiments of the present disclosure are illustrated in the drawings, which are illustrative rather than restrictive. No limitation on the scope of the technology, or on the claims that follow, is to be implied or inferred from the examples shown in the drawings and discussed herein.

Treatment of many dermatological conditions involve using laser light to heat a target skin area to thermally damage a selected structure within the target skin area and promote a healing response. Consistently accurate delivery of energy to targeted structures to achieve a desired level of damage to the target structure, while minimizing the delivery of energy and corresponding damage to non-targeted structures, has remained an unrealized goal. The present disclosure is directed to providing systems and methods to achieve these objectives.

As used herein "target skin area" refers to the skin receiving the energy of a laser pulse. The target skin area may include the surface skin area illuminated by the laser pulse, as well as deeper structures beneath the surface skin area that receive at least a portion of the energy from the laser pulse. As such, "target skin areas" treated by a laser pulse may refer to a volume of skin as opposed to a true area of an outer surface of the epidermis.

As used herein, "surface temperature" in reference to a target skin area refers to the temperature of the target skin area as determined or measured at or above the surface of the skin. In particular, where infrared (IR) energy radiated from a target skin area is used to measure the temperature of the skin surface, the surface temperature determination includes energy radiated from deeper in the epidermis in addition to the outermost layer of cells. Without being bound by theory, the strong scattering effects of IR wavelengths within the epidermis limit the energy emitted and detected to the upper 100 microns, and primarily the upper portions thereof. Consequently, "determining a surface temperature" based on detection of radiated IR energy refers to the determination of a composite or average temperature of the upper portions (e.g., tens of microns in depth) of the epidermis, and not merely the outermost layer of skin cells. In embodiments of the present invention, IR-based temperature measurements or determinations provides a reliable and precise determination of the temperature of the uppermost portion of the epidermis.

As used herein in connection with optical elements and optical energy, "engages" refers to optical contact between optical energy (e.g., a laser pulse or IR energy) and an optical element such as a lens or a mirror. A laser pulse or IR energy may engage a lens by passing through it, and engages a reflective element by being reflected of its surface.

In one aspect, the present invention comprises systems and methods having a handpiece for improved temperature control of a target skin area during the delivery of one or more therapeutic laser pulses in the treatment of a medical condition. The handpiece is configured to facilitate the delivery of laser pulses traveling in a first direction to a target skin area, and to allow IR energy radiated from the target skin area to travel in a second direction generally opposite ("counterdirectional") to the first direction to detect skin temperature. The handpiece is optically coupled to a laser source adapted to generate at least one, and preferably a plurality, of therapeutic laser pulses for application to the target skin area. The handpiece receives therapeutic laser pulses from the laser source, and includes a cooling window for contacting and cooling a first skin area that includes the target skin area. The cooling window is transmissive to the laser pulses and to IR energy radiated from the target skin area. The laser pulses travel through the handpiece along a first optical path in the first direction, and pass through the cooling window to a target skin area within the first skin area. The system further includes a temperature determination unit that includes a temperature sensing element and a processor for determining a surface temperature of the target skin area based on IR energy radiated from the target skin area through the cooling window along a second optical path travelling along a second optical path generally opposite or counterdirectional to the first optical path. In a preferred embodiment, the first optical path and the second optical path share a common optical axis for at least a portion of their length. The handpiece includes a reflective optical element located in the first optical path and having one of a slot and an aperture through which the laser pulses pass while traveling along the first optical path. The reflective optical element is oriented to receive the IR energy radiated from the target skin area along the second optical path, and to reflect it onto the temperature sensing element. The temperature sensing element generates a signal that is processed by the processor to determine the surface temperature of the target skin area. In a preferred embodiment, the reflective optical element is precisely oriented to receive IR energy from substantially only the target skin area, and not from other adjacent tissue within the larger skin area cooled by the cooling window. The handpiece further comprises at least one second optical element within the first optical path, and the laser pulses engage the at least one second optical element. In a preferred embodiment, the at least one second optical element comprises a plurality of optical elements, including at least one lens and at least one reflective element (e.g., a mirror). In a still more preferred embodiment, the IR energy radiated from the target skin area along the second optical path also engages the plurality of optical elements. In various embodiments, the at least one second optical element may comprise elements for focusing, splitting, redirecting, collimating, or performing other operations on the laser pulses and/or IR energy.

In some embodiments, the present invention comprises systems and methods for determining or measuring a surface temperature of a target skin area of a patient during a laser treatment using a handpiece that provides contact cooling of the skin and surface temperature sensing of substantially only a target skin area receiving laser energy. In some embodiments, the present invention provides improved temperature control of a target non-surface (i.e., deeper) structure in the target skin area of a patient during the laser treatment. By providing accurate temperature control of a target skin area during the delivery of laser pulses, the invention provides systems and methods with improved efficacy, safety and/or comfort to patients being treated for a range of dermatological conditions.

In some embodiments, the present invention comprises systems and methods for treating the skin of a patient with therapeutic laser pulses with a handpiece that provides contact cooling of the skin and contact sensing to ensure proper contact between the contact cooling element and skin of the patient. In some embodiments, the handpiece further includes temperature sensing based on IR energy radiated from the target skin area receiving the laser pulse(s) and traveling counterdirectionally to the laser pulses.

In one aspect, the invention provides systems and methods of controlling a temperature of a target skin area during a laser treatment to avoid one or more of overheating or excessively damaging the target area, underheating the target structure, or causing undesired damage to overlying non-targeted structures.

In one aspect, the present invention discloses systems and methods for minimizing the temperature increase of non-target structures overlying a target structure within a target skin area during the delivery of a laser one or a plurality of laser treatment pulses to raise the target structure from a first temperature to a second temperature (e.g., a damage threshold temperature).

In various embodiments, systems of the present invention may determine the temperature of a target skin area one or a plurality of times before, during, or after treatment of the target skin area using IR energy radiated from the skin. The laser treatment may comprise comprises one pulse, or a plurality of pulses comprising a single heating episode of the target skin area. As used herein, a "single heating episode" involves a plurality of pulses where the first pulse raises the temperature of the target skin area from a first or baseline temperature immediately prior to the first pulse, and each successive pulse in the heating episode is applied before the target skin area returns to the first or baseline temperature. Where a plurality of pulses is used to heat the target skin area in a single heating episode, the temperature of the target skin area may be determined during a pulse, between pulses, or a combination of during and between pulses of the single heating episode.

As used in connection with temperature determinations, "real-time" refers to temperature determinations (e.g., temperature measurements or calculations based on data from an IR temperature sensor) performed with little time delay (e.g., less than 100 msec, more preferably less than 5 msec, most preferably 1 msec or less) between the initiation and conclusion of temperature determination. Stated differently, real-time temperature determinations are those made very rapidly and capable of use by the system to perform one or more tasks, such as terminating a treatment of a target skin area, logging the skin temperature profile vs time to a memory, or providing a warning indication to a user.

In one aspect, the invention also comprises contact cooling applied to an external surface of a first skin area to enable heating of deeper structures (e.g., a sebaceous gland) to a damage threshold temperature, while minimizing the heating of overlying non-targeted tissue structures. Real-time temperature determinations may occur during before, during, or after the cooling of a first skin area, and may be used (e.g., by a processor executing a treatment algorithm) to perform a responsive action such as initiating, terminating or adjusting the cooling process, initiating or terminating the delivery of one or more laser pulses to a target skin area within the skin area being cooled, or adjusting a parameter of the laser therapy.

In one aspect, the invention comprises a method of treating a patient having one of more dermatological conditions including, without limitation, abnormal pigmentation conditions, acne vulgaris, dyschromia, hyperhidrosis i.e., excessive sweating), pigmented lesions, vascular lesions, and wrinkles and fine lines by controlled heating of a target skin area from a first surface temperature to a second surface temperature sufficient to cause thermal damage to one or more structures in the target skin area. In one embodiment, the duration of a laser treatment pulse is based on determining the surface temperature of the target skin area one or more times before, during, or after the delivery of laser treatment pulses. In one embodiment, a laser treatment pulse is terminated when the second surface temperature reaches a value indicative of a deeper target structure (e.g., a sweat gland) reaching a desired treatment temperature. The second surface temperature corresponding to the target structure reaching its treatment temperature may be determined prior to treatment, e.g., by thermal (mathematical) modeling of the heating of the target skin area as a function of skin depth based on the parameters of the treatment laser such as wavelength, energy flux, and thermal characteristics of the target skin area such as thermal conductivity, the absorption coefficients of various tissue structures and/or chromophores, etc.

In one aspect, the invention comprises a method of treating a patient having acne vulgaris by controlled heating of a target skin area from a first surface temperature to a second surface temperature, where the second surface temperature corresponds to a temperature resulting in thermal damage to one of sebum or a sebaceous gland within the target skin area. In one embodiment, the duration of the laser treatment pulse is based on determining the surface temperature of the target skin area a plurality of times during the delivery of one or more laser treatment pulses. In one embodiment, the laser treatment pulse is terminated when the second surface temperature reaches a value indicative of the deeper sebaceous gland reaching a sebaceous gland treatment temperature. The second surface temperature corresponding to the sebaceous gland reaching the sebaceous gland treatment temperature may be identified by thermal modeling as previously discussed.

FIG. 1 is a side view illustrating a cross-sectional view of a portion 100 of the skin of a patient, including the outermost epidermis 102, the middle layer or dermis 104, and the bottom layer or hypodermis 106. The epidermis 102 has a thickness of about 80-100 μm, which may vary from patient to patient, and even for a single patient depending upon age, health status, and other factors. It includes up to five sub-layers (not shown) and acts as an outer barrier.

The dermis 104 has a thickness of about 1-5 mm (1000-5000 μm). It contains the blood vessels, nerves, hair follicles, collagen and sweat glands within the skin. Because skin conditions frequently involve structures in the dermis, many laser systems must include sufficient energy to penetrate into the dermis to reach those structures. Careful selection of a number of parameters must be made in the design and construction of laser systems to achieve a desired level of damage to a target structure while minimizing or avoiding damage to non-targeted (e.g., overlying) structures. For example, incorrect selection of the laser wavelength, pulse width, energy per pulse, the use (or nonuse) of a seed laser, or the pump energy of the laser source or amplifier may result in undesired damage and poor performance in treating a dermal structure. Numerous other system choices, such as the use or non-use of an articulating arm for delivery of the laser light to a handpiece for application to the skin, may also affect overall system performance.

The lowest layer of the skin is the hypodermis 106, which includes adipose tissue and collagen. The hypodermis 106 helps control body temperature by insulating the structures of the body below the skin. In addition, the hypodermis protects the inner body tissues from damage by absorbing shock and impacts from outside the body. Because the hypodermis contains fat, its thickness varies widely from person to person based on diet, genetic makeup, and other factors.

FIG. 1 depicts a laser beam 108 applied to a target skin area 110 of the skin 100. The target skin area 110 comprises a surface skin area 112, as well as underlying skin tissue 114 that absorbs at least a portion of the energy of the laser beam 108.

Figure 2:
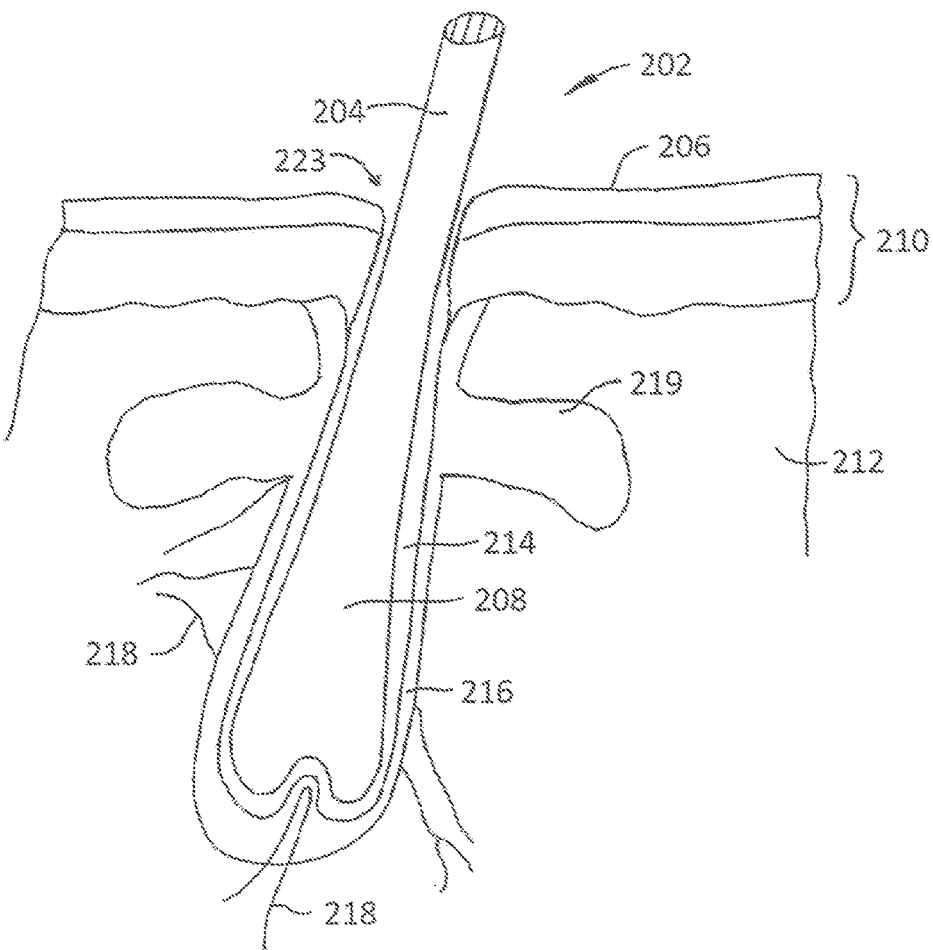
FIG. 2 is a cross-sectional illustration of skin tissue depicting a hair follicle and a sebaceous gland.

FIG. 2 is a side view of the skin of a patient illustrating in simplified form, a hair 202 including a hair shaft 204 extending beyond the exterior skin surface 206. Hair shaft 204 includes a root 208 located below epidermis 210 in the dermis 212. The base, or papilla, of root 208 is located about 4 mm below exterior skin surface 206. Root 208 is housed within hair follicle 214 and is surrounded by tissues including connective tissue sheath 216 and blood vessels 218. Follicle 214 includes a sebaceous gland 219 below an opening 223. Sebaceous glands such as gland 219 are typically located at depths ranging from about 0.3 mm (300 µm) to about 2.0 mm (2000 µm) below exterior skin surface 206, but their depth varies depending upon body location.

Epidermis 210 includes melanin (not shown), a dark pigment found in tissues of the hair, skin and eyes. Melanin, the primary determinant of skin color, is located within globular structures known as melanosomes, which are produced by skin cells called melanocytes. Darker skin has more melanosomes (and thus more melanin) per unit skin area compared to lighter skin. Laser systems targeting deeper structures such as sebaceous gland 219 in the dermis may present a higher risk of patient discomfort where wavelengths having a relatively high absorption coefficient in melanin are used. Without being bound by theory, when laser light at wavelengths readily absorbed by melanin is applied to darker skin (or dark tattoos having ink particles that absorb laser light at similar wavelengths to melanin), the energy absorbed by the melanin (or tattoo ink particles) attenuates part of the laser energy that otherwise would reach deeper structures, heating the skin of the epidermis and/or upper dermis to a greater degree than lighter/un-tattooed skin. Additional energy—e.g., using higher fluences, higher energy per pulse, or longer treatment times—must be applied to reach and heat deeper structures to a target treatment temperature. However, higher pulse fluences and pulse energy may compound the problem, since the additional energy delivered in a shorter time period will cause the overlying skin temperature to rise even faster than using lower fluences or energies. In addition, longer treatment times can only deliver more energy to the target if the energy is delivered within the TRT of the target tissue—otherwise, the additional energy largely leaks from the target tissue into adjacent non-target tissue.

Accordingly, in one aspect, the present invention provides laser treatment systems to minimize discomfort by adjusting one or more treatment parameters based on the patient's skin type. In one embodiment, the invention provides systems and methods comprising a handpiece for determining a skin type of a patient and automatically adjusting one or more treatment parameters based on the skin type of the patient. This may involve, for patients having darker skin types, one or more of: providing additional cooling of the patient's skin prior to applying a laser therapy to the patient's skin; lowering a first skin temperature at which a therapy pulse is initiated and applied to the patient's skin; lowering a fluence of a laser therapy; lowering a peak power of the laser pulses of a laser therapy; providing a longer pulse width of a pulsed laser therapy; and providing a larger beam diameter for a pulsed laser therapy.

Successful treatment of acne involves damaging sebocytes, sebum and/or sebaceous glands. This involves heating these structures to damage the gland and/or kill bacteria resident therein. Accordingly, in one embodiment the invention provides laser light at a wavelength that is highly absorbed by sebum, compared to competing skin chromophores (e.g., water), to limit the damage to non-targeted tissue and concentrate the laser energy delivered into the targeted sebaceous gland. Because sebaceous glands are relatively deep structures located in the dermis at depths of 300-2000 µm (0.3-2.0 mm), it is desirable to select a wavelength of light capable of non-ablative penetration to these depths.

Figure 3A:
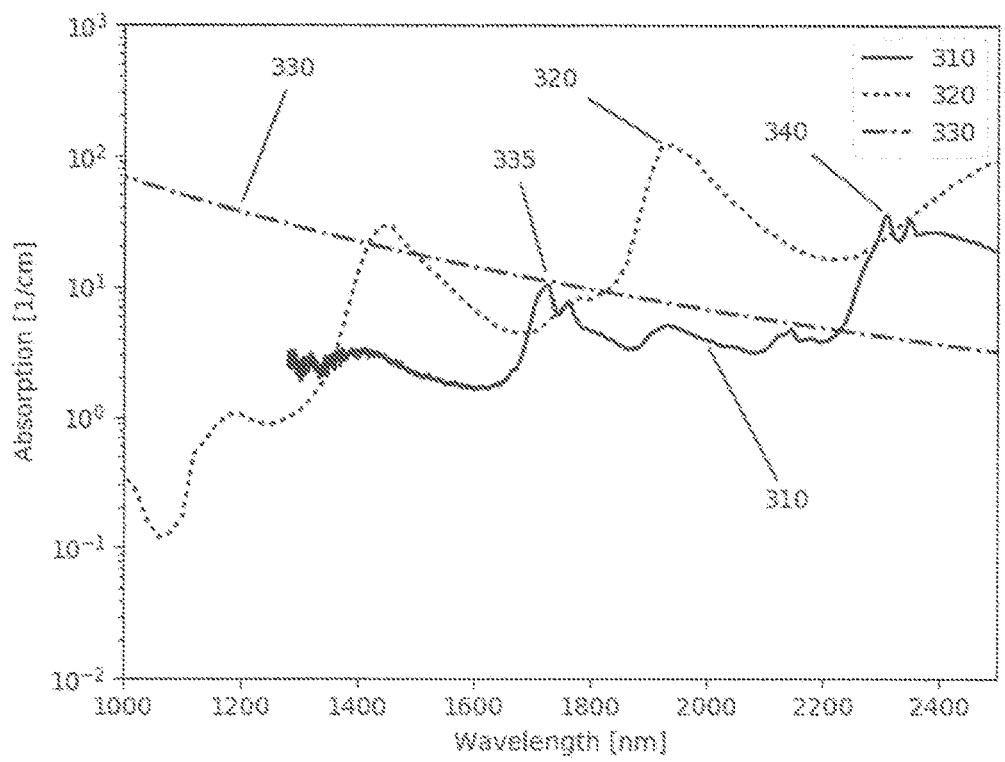
FIGS. 3A and 3B are graphs illustrating the absorption coefficients of human sebum lipid, water, and melanosomes for various wavelengths of light.
Figure 3B:
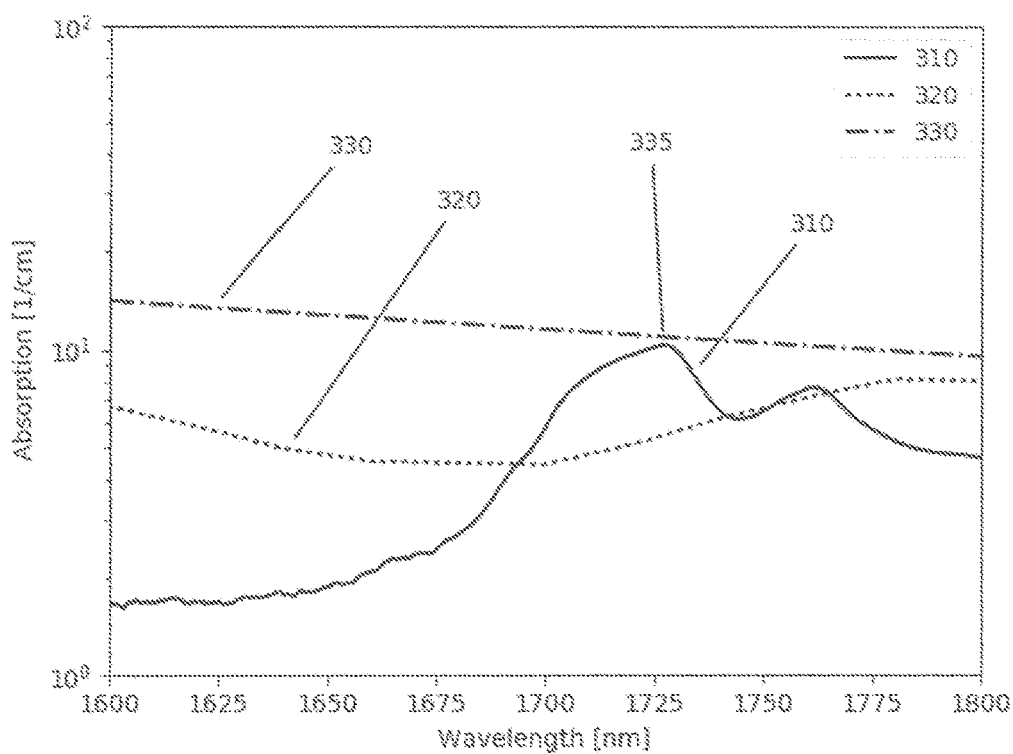

FIGS. 3A and 3B are graphs illustrating the absorption curves for several chromophores of interest (water, sebum, and melanosomes) at wavelengths of light for portions of the near-infrared spectrum (about 750 nm-1400 nm) and the short-wavelength IR spectrum (about 1400-3000 nm). The figures highlight the problem of targeting tissues having a target chromophore with poor selectivity relative to a non-target chromophore in a nontarget tissue. FIG. 3A illustrates the absorption curve 310 for sebum, the water absorption curve 320, and the absorption curve 330 for melanosomes. It will be appreciated that in laser treatment systems directed toward conditions other than acne, e.g., tattoo removal or pigmented lesions, the absorption of other chromophores (e.g., inks of various colors, hemoglobin, etc.) will be important considerations in selecting laser treatment system parameters such as wavelength, fluence, peak power, etc.

For much of the wavelength range of FIG. 3A, the water absorbs light more strongly that sebum, as illustrated by the absorption curve for water 320 lying above the sebum absorption curve 310 for most of the wavelength range. However, the sebum absorption curve 310 has a peak at about 1727.5 nm (point 335), meaning that sebum absorbs laser light at this wavelength more strongly than light at other nearby wavelengths, e.g., 1650 nm or 1800 nm. Although the absorption coefficient for sebum in this wavelength range is greater than that of water, the ratio of the two curves in this region has a maximum value of about two. As previously noted, ratios less than ten are one characteristic of poor chromophore selectivity. The other characteristic of tissues with poor chromophore selectivity is that the target chromophore absorption coefficient only exceeds that of the non-target chromophore for a narrow range. The absorption coefficient of water (curve 320) is less than that of sebum in a range of from about 1693 nm to about 1742 nm. Since this range is less than 6000 GHz, the sebum curve in this wavelength is an example of poor chromophore selectivity. Note that there are no areas of the sebum curve 320 exceeding the absorption curve for water at which the ratio of the sebum and water coefficients is 10 or greater. Accordingly, treating acne with laser light is characterized by poor chromophore selectivity even at the most advantageous wavelength.

The absorption coefficient of melanosomes exceeds that of sebum at all wavelengths less than about 2225 nm, although only by a small amount at the 1727.5 nm peak for sebum, as demonstrated at point 335 of FIG. 3A, where the two absorptions curves approach one another. It will be appreciated by persons of skill in the art that the concentration of sebum, water, and melanin may vary from patient to patient for a given area, and even within a particular patient depending upon the target tissue structure(s), the hydration status of the patient, and the skin type or area of the patient.

As shown more clearly in FIG. 3B, which is a more detailed illustration of the absorption curves of FIG. 3A for the 1600-1800 nm wavelength region using like numbers for like absorption curves and peaks, the absorption coefficient for sebum (curve 310) at a peak of about 1727.5 nm (point 335) is approximately twice that of water (curve 320), and is only slightly less than that of melanosomes (curve 330). Specifically, the absorption coefficient for melanosomes at 1727.5 is about 11.0 cm−1, and that of sebum is about 10.3 cm−1. As can be seen from steep drop in curve 310 on either side of the peak, the ratio of the sebum and water coefficients declines relatively rapidly on either side of the peak. For typical diode lasers having a relatively broad linewidth, much of the laser energy will be provided at ratios significantly less than the maximum value, further contributing to heating of non-target tissues overlying the sebaceous gland. There is a need for laser treatment systems incorporating laser sources with reduced linewidth to treat tissues (such as sebum in FIGS. 3A and 3B) having poor chromophore selectivity. FIGS. 12-15 discuss structures and methods to achieve a narrower linewidth, preferably less than 500 GHz, more preferably less than 300 GHz, more preferably still less than 200 GHz. Accordingly, in one embodiment, the invention comprises a laser providing pulsed laser light at a wavelength of between 1693-1742 nm, more preferably at about 1720-1730 nm, and more preferably still at about 1727.5 nm.

Referring again to FIG. 3A, the sebum absorption curve 310 has a further absorption peak (340) of about 2305 nm, exceeding that of both water and melanosomes at the same wavelength. In one embodiment, the invention comprises a laser providing pulsed laser light at a wavelength of between about 2287-2318 nm. Although sebum strongly absorbs light at 2305 nm, light at this wavelength is less suitable because its penetration depth into skin is much less than that of light at 1727.5 nm. In general, at wavelengths shown in FIGS. 3A and 3B, the penetration of light decreases with increasing wavelength. Treatment of acne and other conditions with laser light involves multiple tradeoffs, including the relative absorption coefficients of target and non-target tissues/structures, penetration depth of the wavelength of interest into skin, laser power, laser pulse fluence, pulse duration, pulse frequency, etc.

Figure 4A:
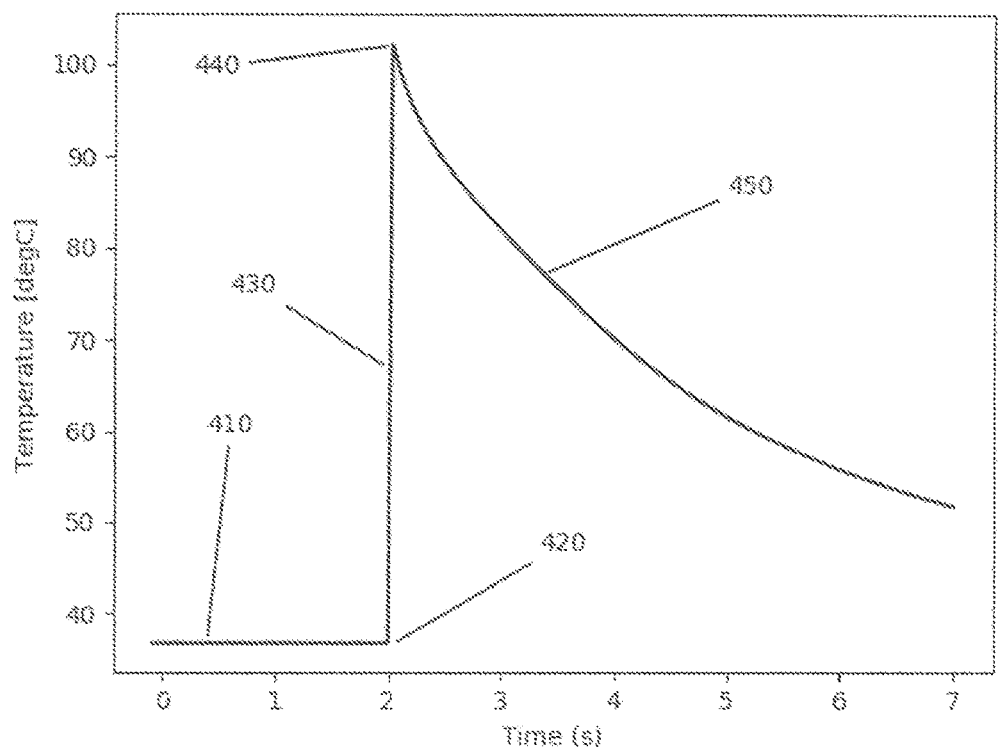
FIG. 4A is a graph illustrating a surface temperature profile of a target skin area according to a mathematical model of a treatment with a laser pulse.
Figure 4B:
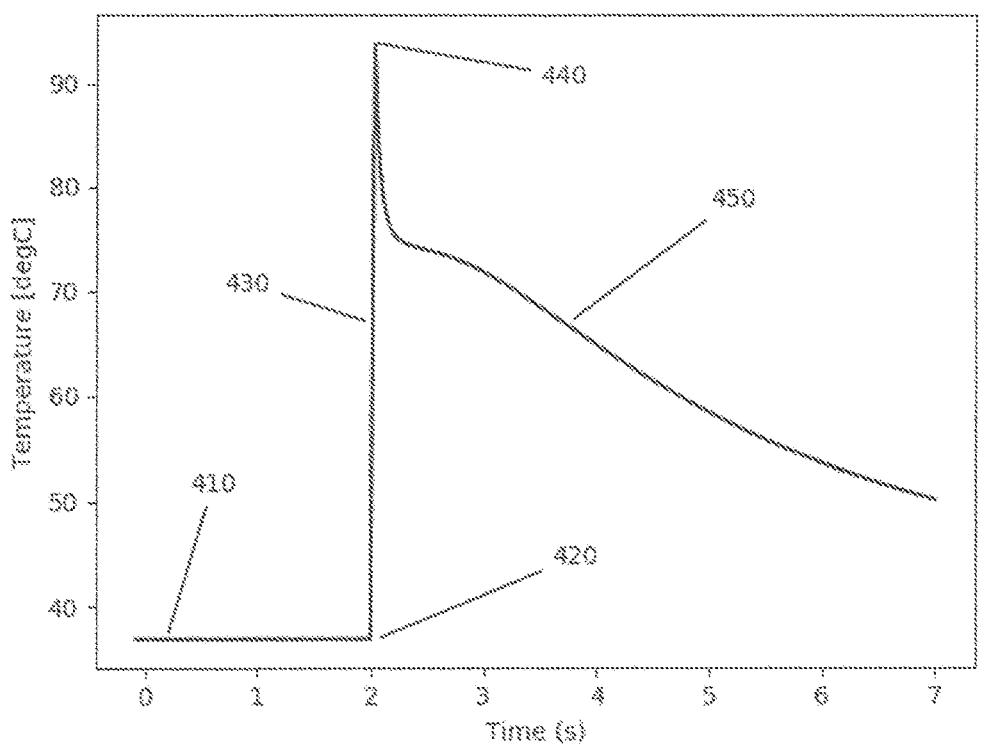
FIG. 4B is a graph illustrating a sebaceous gland temperature profile within a target skin area according to the mathematical model of the laser pulse of FIG. 4A.

FIGS. 4A and 4B illustrate exemplary temperature profiles of the surface of a target skin area (FIG. 4A) and a sebaceous gland (FIG. 4B) located below the surface of the target skin area during a laser pulse according to a mathematical model. The laser pulse is intended to raise the temperature of the sebaceous gland to a temperature to achieve a desired cell population death for sebocytes. In this embodiment, the laser pulse is a tophat pulse (i.e., having a uniform intensity profile over the covered area) with a wavelength of 1727.5 nm, a pulse duration of 30 msec, a beam diameter of 2.8 mm, a power of 75 W, a pulse energy of 2.25 J, and a fluence of 37 J/cm2. For purposes of illustration, the skin is depicted as remaining at body temperature for 2 seconds prior to the application of the pulse, although it will be appreciated that any arbitrary time period could be shown.

Referring to FIG. 4A, at time t=2 seconds, a single pulse of laser light having the parameters noted above is initiated and applied to a target skin area, depicted at point 420. The surface temperature of the skin rises during the pulse, as shown by line 430, to slightly above 100° C. as shown by peak 440. After the pulse is terminated, the skin surface temperature of the target area cools rapidly over the next several seconds, as indicated by curve 450, falling to below 60° C. within 4 seconds (t=6 seconds) after the termination of the pulse.

FIG. 4B illustrates the temperature profile of a sebaceous gland located at a depth of 650 μm below the skin surface in the laser pulse model of FIG. 4A. As in FIG. 4A, the skin remains at body temperature for 2 seconds (410) prior to the initiation of a single pulse (421) applied to the target skin area. The temperature of the gland rises during the pulse (430) to a maximum temperature 440 of about 92° C.—less than the surface skin temperature illustrated in FIG. 4A due to scattering and the energy absorbed by the overlying tissue. Because the pulse energy at 1727.5 nm is preferentially absorbed by the sebaceous gland (as discussed in connection with FIGS. 3A and 3B), comparatively more energy from the laser pulse that reaches the gland is absorbed by the oily tissue therein compared to overlying tissue containing a higher water content. Consequently, the temperature profile (450) of the sebaceous gland after termination of the pulse at 440 differs significantly from that of the skin surface temperature depicted in FIG. 4A. Although the temperature initially falls rapidly to about 85° C., the temperature thereafter falls more slowly than the surface temperature shown in FIG. 4A.

The pulse modeled in FIGS. 4A and 4B has energy levels below those necessary to ablate skin tissue. Although the pulse will result in thermal damage to the sebaceous gland and could be used to treat acne, temperatures above 45-50° C. are likely to result in significant discomfort when they persist, as illustrated in FIG. 4A, for 4 seconds or longer. Accordingly, the pulse depicted in FIG. 4A would have limited application as a viable treatment to most patients. In one embodiment, the laser pulses described in connection with FIGS. 4A and 4B result in temperatures too high to be used for treatment, although they could be modified (e.g., by lowering pulse fluences, shortening pulse treatment times, etc.) to result in skin temperatures more suitable for treatment. In one embodiment, temperatures may be lowered by skin cooling, as described in connection with FIGS. 5A and 5B.

Figure 5A:
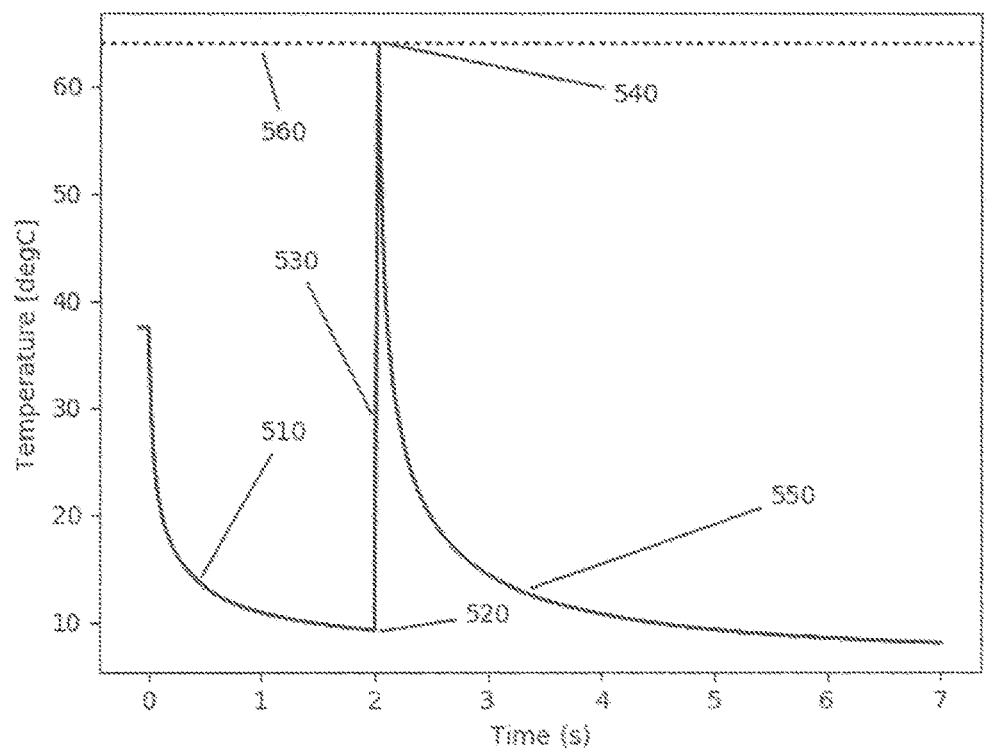
FIG. 5A is a graph illustrating a surface temperature profile of a target skin area before, during, and after a laser pulse treatment with skin cooling, according to a mathematical model.
Figure 5B:
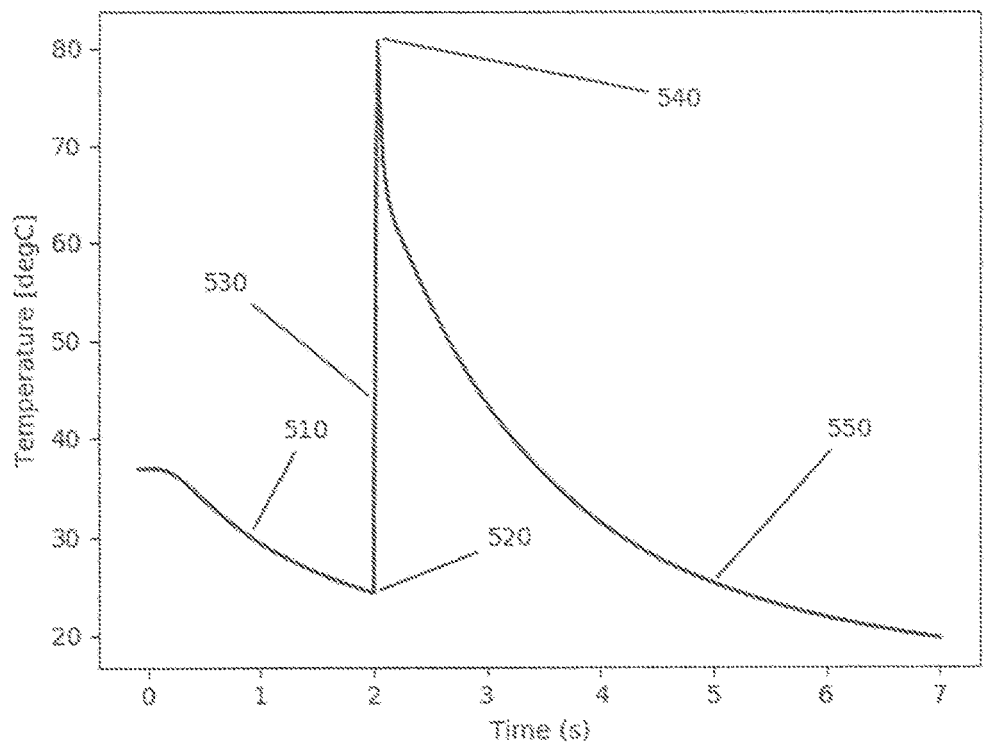
FIG. 5B is a graph illustrating a sebaceous gland temperature profile within a target skin area before, during, and after a laser pulse treatment with skin cooling, according to the mathematical model of FIG. 5A.

FIGS. 5A and 5B illustrate exemplary temperature profiles of a target skin area during a laser pulse according to a different mathematical model than those of FIGS. 4A-B. In the embodiment of FIGS. 5A and 5B, the laser pulse has the same parameters as those of FIGS. 4A-B (wavelength λ=1727.5 nm; pulse duration=30 msec; beam diameter=2.8 mm, power=75 W; pulse energy=2.25 J; fluence=37 J/cm2). However, in FIGS. 5A and 5B the target skin area is cooled prior to, during, and after the application of the laser pulse.

Although many known methods and modes of precooling the skin may be used, the embodiment of FIGS. 5A and 5B are modeled on a system having a contact cooling element applied to a first skin area that includes a target skin area to be treated by the laser pulse. The contact cooling element includes a cooling window that, in some embodiments, directly contacts the first skin area, and the target skin area actually irradiated by the laser pulse is wholly located within the first skin area. Although a variety of materials may be used as the contact cooling window, in the embodiment of FIGS. 5A and 5B, the cooling system includes a sapphire cooling window cooled by a thermoelectrical cooler (TEC) coupled to the window. The sapphire cooling window has a thickness of 3 mm and a diameter of 1 inch (25.4 mm), although many different sizes, shapes, thicknesses, and materials may be used different embodiments. For example, although the cooling window modeled in the embodiment of FIGS. 5A and 5B was circular, other cooling window shapes such as square, rectangular, or other polygonal or nonpolygonal shapes could be used in different embodiments and for different tissue types. The cooling window was modeled as being cooled to a temperature of 5° C.

In alternative embodiments, non-contact cooling systems (e.g., cold air or other fluid circulated onto or across the surface of a target skin area) may be used to cool the skin. However, it is believed that the thermal resistivity of the skin, and the thermal coupling between the skin and gases such as air, typically preclude non-contact systems from providing adequate cooling capacity during the delivery of laser pulses to both effectively treat deeper target structures and prevent the skin surface from reaching temperatures likely to result in significant discomfort. Accordingly, contact cooling systems are preferred. In other embodiments, evaporative cooling systems (e.g., sprayed coolant evaporating from the skin) may be used.

In FIG. 5A, the contact cooling element at 5° C. is applied to the skin at time t=0, and skin temperature falls rapidly along curve 510 to a target temperature of about 10° C. at time t=2 second, at which point (520) the laser pulse is applied to the skin. Delivery of the laser pulse to the target skin area is continued until a target surface temperature 560 of the target skin area is reached (540), at which point the laser pulse is terminated. Because the contact cooling element continues to cool the skin both during and after the laser pulse, the surface temperature falls rapidly along curve 550 after laser pulse termination.

FIG. 5B illustrates the temperature profile of a sebaceous gland located at a depth of 650 μm below the skin surface in the cooling and laser pulse delivery process of FIG. 5A. When contact cooling is applied to the skin at time t=0, the temperature of the gland declines (curve 510), but much less rapidly than the surface temperature, depicted in FIG. 5A. The laser pulse is initiated at point 520, and the temperature of the gland rises along line 530 until the laser pulse is terminated (540). The gland temperature thereafter falls along line 550, but less rapidly than the surface temperature decline following the pulse termination in FIG. 5A.

Because direct measurement of the gland temperature is difficult or impossible given its depth within the skin, in embodiments of the present invention, surface skin temperature may be monitored as an indirect indication of the gland temperature. Because the goal of the laser treatment is to heat the sebaceous gland to a damage threshold temperature, cooling the gland (as opposed to the skin surface) shown by curve 510 in FIG. 5B is undesired, but is an unavoidable consequence of the protective precooling of the overlying skin tissue. Precooling the overlying skin tissue to a desired surface temperature of about 10° C., as shown in FIG. 5A, generates a downward cooling wave in the target skin area, propagating from the skin surface toward the deeper tissues in the dermis and hypodermis. The precooling process may be controlled such that, for a sebaceous gland in a known depth range, when the laser pulse is delivered to heat the target skin area, the precooled overlying skin remains below a damage threshold temperature while the target sebaceous gland reaches (or exceeds) a damage threshold temperature. This is facilitated by selecting a laser wavelength for which the absorption coefficient of sebum/sebaceous gland tissue exceeds that of water, the primary chromophore of most of the overlying dermal and epidermal tissue.

Comparing FIGS. 5A and 5B, precooling the skin allows the sebaceous gland to reach a temperature of about 78° C. at the termination of the laser pulse—about 13° C. above the surface temperature of target skin area at the surface (about 62° C.). Although the overlying tissue is unavoidably heated during pulse delivery, careful precooling before initiating the laser pulse allows the surface temperature to be precooled to a temperature well below the sebaceous gland at pulse initiation (about 10° C. for the skin surface vs. about 22° C. for the sebaceous gland as shown by FIGS. 5A and 5B at point 520). This temperature difference occurs because the cooling window creates a thermal gradient between the skin surface and deeper structures as heat is removed. In addition, the pulse energy at a wavelength of 1727.5 nm is more highly absorbed by the sebaceous gland than overlying tissue. Because of the selective precooling and differential absorption between the surface and the sebaceous gland, the non-targeted overlying tissue is heated by the laser pulse to a lower temperature (about 63° C., FIG. 5A at point 540) than the targeted sebaceous gland (about 81° C., FIG. 5B at point 540), minimizing damage to the non-targeted tissue and patient discomfort.

Figure 5C:
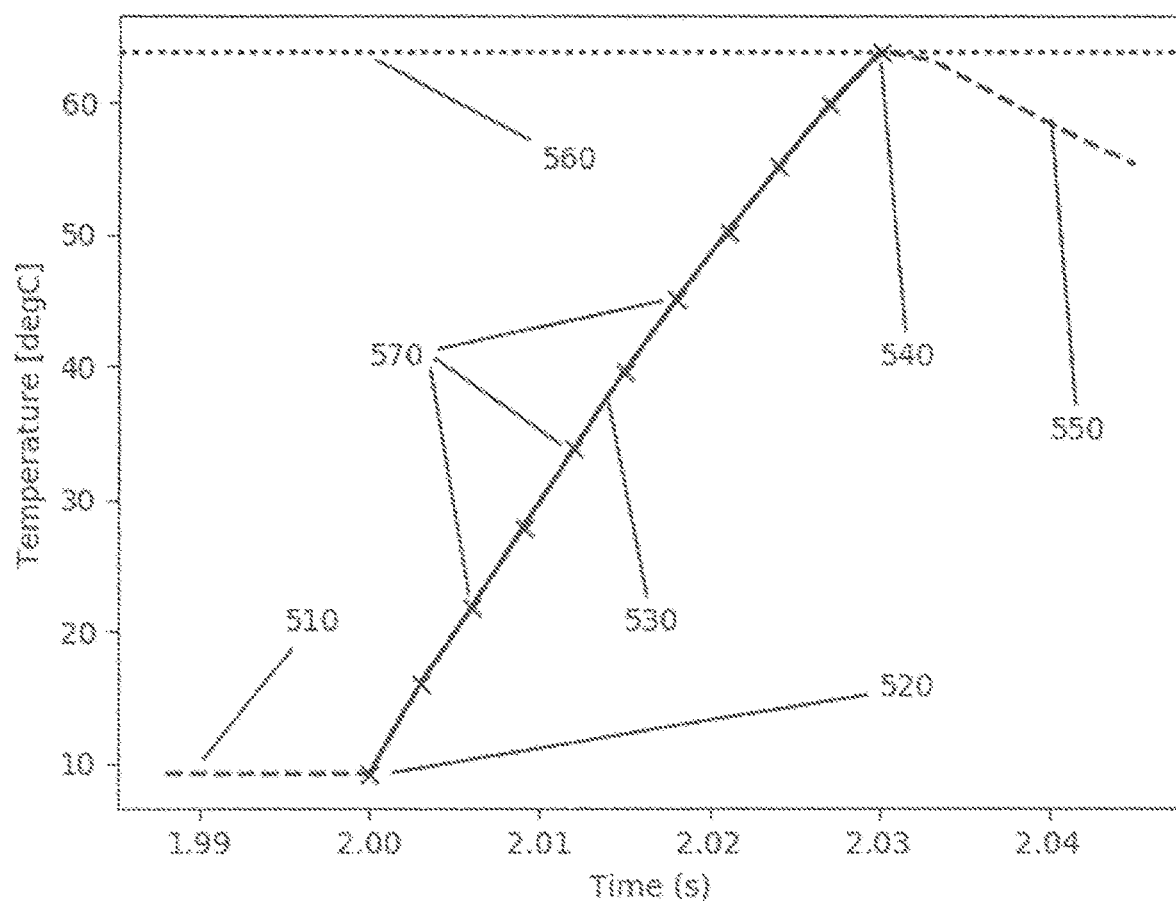
FIG. 5C is more detailed graph illustrating a surface temperature profile for a target skin area during treatment with a laser pulse according to the mathematical model of FIG. 5A.

In some embodiments, the present invention includes a method of controlling the duration of a pulse to limit the surface temperature of a target skin area to a desired or target threshold using a handpiece capable of contact cooling and rapid, real-time temperature measurement of the skin during the delivery of one or more laser pulses. FIG. 5C demonstrates a method of achieving such control by monitoring the temperature of a pulse during the delivery of a single pulse. The surface temperature of the skin may be determined one or more times during pulse delivery, and the pulse may be terminated based on one or more of the skin temperatures. In one embodiment, the skin temperature is periodically determined during the pulse delivery, and the pulse is terminated when the surface skin temperature reaches (or is within a desired interval of) a threshold temperature.

FIG. 5C, illustrates a surface temperature profile during the delivery of the laser pulse of FIG. 5A. From time t=1.99 to t=2.00 seconds, the temperature of the skin near the surface (modeled in FIG. 5C at a depth of 100 μm) is relatively constant at about 10° C. (line 510). At time t=2.00 seconds (520), the pulse is initiated and applied to the skin through the cooling window. Simultaneously, the first of a plurality of surface temperature determinations of the target skin area 570 is made. Pulse delivery continues along line 530, and the surface temperature rises until the pulse is terminated at 540. After pulse termination, the surface temperature falls as indicated by line 550. During pulse delivery, multiple temperature determinations 570 are made at equal intervals, although the frequency of temperature sampling may vary based on a variety of factors such as the time frame desired for heating the tissue, thermal relaxation time of the target structure, pulse fluence, pulse power, pulse wavelength, and exogenous factors such as the target structure damage threshold, and other factors. Temperature determinations may be performed at a desired sampling interval, e.g., 100 msec or less (i.e., 10 or more temperature determinations per second) and may occur at uniform or non-uniform time intervals, e.g., varying based on the difference between a measured temperature and a desired threshold, or on other exogenous factors. In one embodiment, the temperature sampling interval is increased as the surface skin temperature approaches a desired temperature. Depending upon the sensing element and processor used, the surface temperature may be determined at a sampling or time interval of 0.001-100.0 msec (i.e., 1-100,000 psec, or performing 10 to 1 million temperature determinations per second).

FIGS. 5A and 5B illustrate methods of treating a sebaceous gland according to one embodiment of the present invention. Additional details of treating a sebaceous glans may be found in U.S. Pat. No. 10,864,380, which is incorporated herein by reference. However, embodiments of the present invention may be used to treat other structures in the dermis or hypodermis (e.g., sweat glands, hair follicles, etc.) by facilitating precise control of surface and deeper temperatures within a target skin area.

Figure 6:
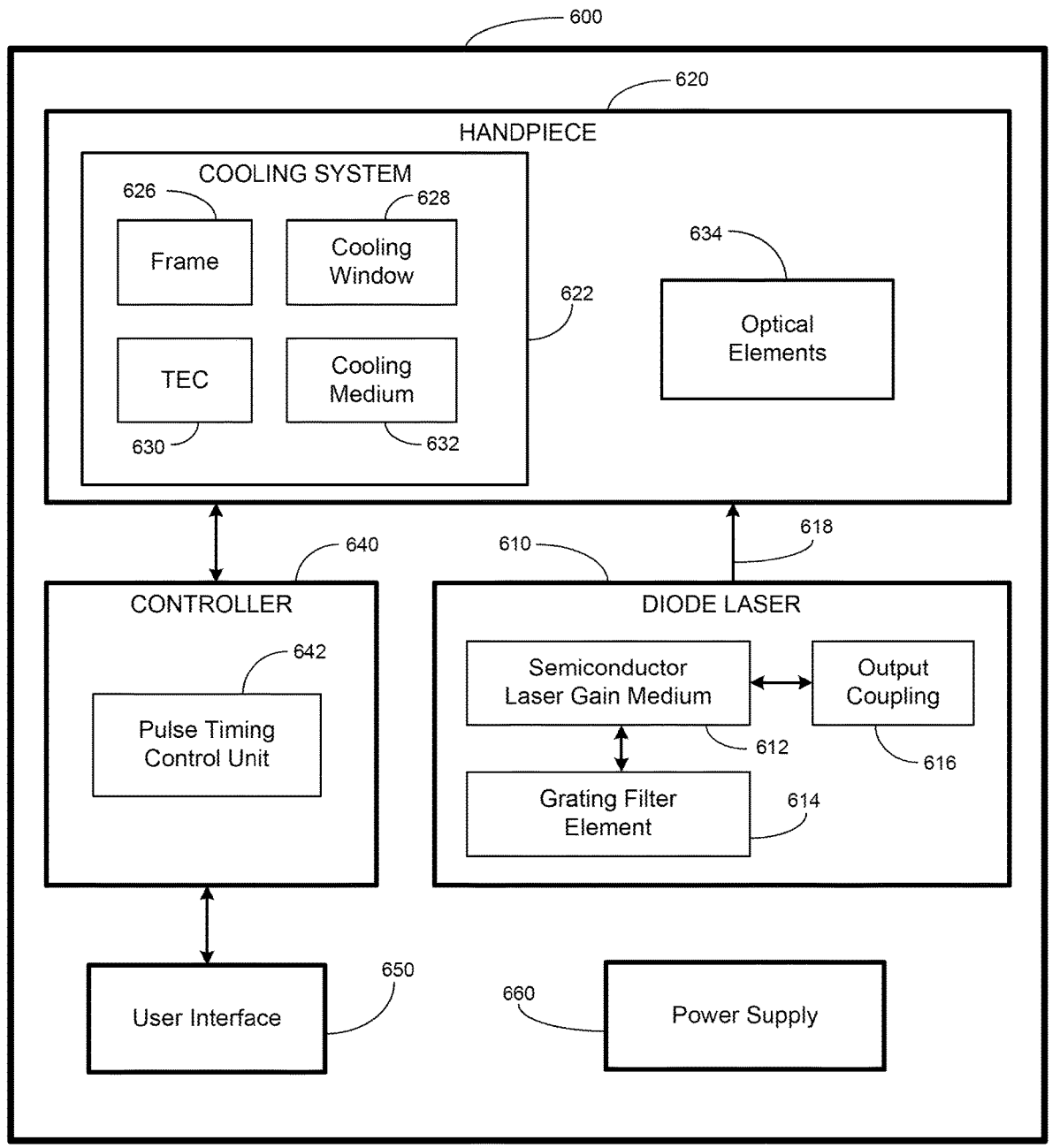
FIG. 6 is a block diagram of an embodiment of a dermatological treatment system according to the present invention.

FIG. 6 is a schematic illustration, in block diagram form, of an embodiment of a therapeutic laser system 600 having a handpiece with contact cooling and temperature sensing for providing therapeutic laser pulses along a first optical path that is coaxial with a second optical path for sensing skin temperature for at least a portion of the first and second optical paths. A laser 610, which is preferably a semiconductor laser, provides laser pulses having a wavelength with a high absorption coefficient in a target tissue. The target tissue may be sebaceous gland tissue, sweat gland tissue, fat, or other tissue. Laser 610 is optically coupled, e.g., by an optical fiber, articulating arm, or other optical coupling elements known in the art, to a handpiece 620 for delivery of one or more laser pulses to a target skin area. Although semiconductor (e.g., diode) lasers are preferred, it will be appreciated that other laser types (e.g., fiber lasers, dye lasers, etc.) may be used in different embodiments.

In a preferred embodiment, the laser source incorporates a grating element to reduce linewidth by amplifying only photons at a desired wavelength. FIGS. 8A-D illustrate laser sources that may be used in systems of the present invention.

Handpiece 620 includes a cooling system 622 for cooling a first skin area that includes a target skin area within the first skin area. Cooling system 622 includes a contact cooling element comprising a cooling window 628 maintained in a fixed position in contact with a heatsink portion of a thermoelectric cooler (TEC) 630 by a window frame 626. Cooling window 628 may comprise any of a variety of IR-transmissive materials, including sapphire, ZnS, diamond, ZnSe, and other thermally conductive material that are transmissive to infrared light. In alternative embodiments (not shown), the contact cooling element may comprise components or structures in addition to cooling window 628, such as a copper (or other material having a high thermal conductivity) cooling element that is not light-transmissive to provide additional cooling capacity.

TEC 630 may be a Peltier-type cooler and has a warm side and a cold side (not shown). The heatsink portion of the TEC 630 is part of the cold side and is used to remove heat from the cooling window 628 to maintain the cooling window at desired temperature as it contacts the first skin area. A cooling medium 632 removes heat from the hot side of the TEC 630 to prevent heat buildup in handpiece 620. In one embodiment, the cooling medium comprises circulating cold water, although other thermally conductive fluids or other materials may be used in different embodiments. In preferred embodiments, the cooling medium is circulated to and from TEC 630 from a reservoir (not shown) that is not part of the handpiece.

To ensure efficient skin cooling, it is necessary to maintain good contact between the skin and the cooling window 628 during treatment. In one embodiment, the invention comprises a laser treatment system including a handpiece having one or more contact sensing elements to detect when the cooling window 628 is properly in contact with the first skin area. The contact sensing elements may determine one or more contact parameters such as contact, force, or pressure. In one embodiment, a safety interlock may be provided to prevent the delivery of laser pulses to the skin of the patient unless one or more contact parameter conditions are fulfilled (e.g., all contact elements in contact with the skin, and/or a threshold force such as 0.5 pounds is being applied to the skin, and the conditions must be satisfied during the delivery of each laser pulse). The contact sensing element(s) may be coupled to, or separate from, cooling window 628 and/or frame 626 (e.g., a heatsink surrounding the cooling window periphery), and may comprise, e.g., one or more electrical contacts capable of sensing electrical activity, conductivity, or resistance of the skin indicative of adequate contact between the skin and the handpiece (e.g., cooling window). Other contact sensing elements (e.g., ultrasonic sensors) detecting different skin parameters associated with proper contact (e.g., force, vibration, pressure, temperature, the presence of sweat or skin oils) may also be used.

One or more skin contact indicators (not shown) may alert a user to the contact status between the skin and cooling window 628. The skin contact indicator may indicate when the contact element(s) are—or are not—in good contact with the first skin area and may prompt the user to manipulate the handpiece to restore good contact when necessary. The skin contact indicator(s) may comprise, e.g., an LED indicator on handpiece 620 that displays a first color when good skin contact exists and a second color when the window 628 is not in proper contact with the skin. Other indicators, such as an audible sound or alarm, may also be provided, and the system may be interlocked such that the system will not apply (or will terminate) a laser pulse if good contact between the cooling window 268 and the skin is absent.

Handpiece 620 may in some embodiments further includes a temperature determination unit (TDU) for determining a surface temperature of the target skin area. The TDU may, in various embodiments, sense the temperature of the target skin area one or more times before (e.g., during a precooling step), during, or after (e.g., during a postcooling step) laser pulse delivery. During delivery laser pulse(s) to a target skin area, the skin surface temperature may be influenced by two different heating mechanisms, including energy absorbed directly from the laser, and thermal bloom resulting from energy conducted from deeper skin tissue as the thermal energy absorbed by deeper structures relaxes into the environment. Thermal bloom from deeper structures back to the skin surface may be a significant cause of epidermal damage in laser systems targeting relatively deep structures such as sebaceous or sweat glands. Therapeutic laser systems such as system 600 enable improved treatment outcomes by ensuring that the surface temperature of a target skin area remains below a desired surface temperature even while heating deeper structures to higher temperatures, minimizing both skin damage and patient discomfort.

The TDU may comprise a temperature sensing element for generating a first signal indicative of skin surface temperature, and a processor for processing the first signal to determine the surface temperature. The TDU may sense the surface temperature of the target skin area one or more times before, during, or after delivery of laser pulse(s) from laser 610. The TDU may be capable of sensing the surface temperature of the target skin area at from 10 to 1 million times per second. In one embodiment, the temperature sensing element of TDU comprises an infrared (IR) radiation detector to detect IR energy radiating from the surface of the target skin area through the cooling window 628, and a processor (e.g., controller 640 as discussed below) to determine the surface temperature of the target skin area based on data received from the TDU. It will be appreciated that non-IR temperature sensors (e.g., an electrical temperature sensor) may also be used. In the embodiment of FIG. 6, the TDU may be a part of the handpiece 620, while in other embodiments, the temperature sensing element, the processor, or the entire TDU may be located outside the handpiece. In preferred embodiments, an IR temperature sensing element is provided as part of the handpiece 620. Additional details about the TDU may be found in co-pending application U.S. application Ser. No. 17/120,237, filed 13 Dec. 2020, which is hereby incorporated by reference in its entirety.

Handpiece 620 also includes a plurality of optical elements 634 to sequentially direct laser pulses along a first optical path within the handpiece to a target skin area, and to direct IR energy from the target skin area along a second optical path that is coaxial with and generally counterdirectional to the first optical path for at least a portion of both optical paths. Additional details on embodiments of the optical elements are provided in connection with FIGS. 7A-B and in the aforementioned '237 application. To facilitate the counterdirectional flow of laser and IR energy, the handpiece comprises a first optical element (not shown) having a first open area through which the first optical path passes, i.e., the laser pulses do not engage the first optical element, and pass through the first open area. In contrast to the laser pulses, however, the IR energy does engage the first optical element, which is preferably a reflective optical element (e.g., a mirror). The first optical element directs the IR energy from the target skin area to the temperature sensing element in the TDU. The signal from the temperature sensing element is processed to determine skin surface temperature at a desired rate of from 10 to 1 million times per second.

The plurality of optical elements 634 in handpiece 620 also includes at least one second optical element (not shown), and more preferably a plurality of second optical elements, that are engaged by the laser pulses and/or IR energy from the target skin area. In one embodiment, shown in more detail in FIGS. 7A-7B, the at least one second optical element comprises eight (8) optical elements, with the first optical path (i.e., the laser pulse path) engaging all eight optical elements, and the second optical path engaging five of the optical elements in addition to the first optical element. The optical elements may include one or more of lenses (e.g., plano-convex lenses, turning mirrors, meniscus lenses, aspherical lenses, flat lenses, etc.), mirrors (e.g., aspherical mirrors), or other optical elements (e.g., optical parametric oscillators) to direct the laser pulses received from the optical laser source (e.g., via an optical fiber cable) to a target skin area. In preferred embodiments, the at least one second optical element comprises a plurality of lenses (e.g., at least three lenses) and at least one mirror, and the first and second optical paths engage at least two lenses and the last least one mirror. The optical elements 634 may in various embodiments concentrate the laser energy to a single target skin area, or may include beam-splitting elements to split each pulse beam into multiple beams to treat a plurality of target skin areas simultaneously.

In one embodiment, the plurality of optical elements 634 includes a movable scanning mirror capable of movement to direct laser pulses to different target skin areas within a first skin area cooled by cooling window 628. The movable scanning mirror also limits IR energy received by the TDU to IR energy from substantially only the target skin area to which the laser is directed at any given time, i.e., it eliminates IR light from other skin areas within the larger first skin area cooled by cooling window 628, which is significantly larger than a single target skin area. In embodiments including a movable scanning mirror, after a first target skin area is treated by one or more laser pulses, the scanning mirror is repositioned to direct subsequent pulses to a new (i.e., second, third, etc.) target skin area within the larger first skin area cooled by the cooling window 628. When a desired number of target skin areas have been treated at a single cooling window position, the user may reposition the cooling window 628 to a new position covering a new skin area, and a different group of target skin areas within the new skin area may be treated by laser 610 using scanner in handpiece 620. In one embodiment, the position of the movable scanning mirror may be adjusted on two or more axes, e.g., by one or more motors, thereby directing succeeding pulses to different target skin areas within the first skin area, enabling treatment of a relatively high proportion of the total area in contact with the cooling window. In alternative embodiments, the plurality of optical elements 634 may not include a scanner. Additional details on the use of a scanning mirror may be found in the '237 application previously noted.

Referring again to FIG. 6, system 600 further includes a controller 640, which may comprise one or more processing elements such as microprocessors, microcontrollers, field programmable gate arrays (FPGAs), etc. to control the operations of the laser treatment system. Controller 640 includes a pulse timing control unit 642 that controls the timing of the laser pulses from laser 610, including initiating the pulse at a first timepoint and terminating the pulse at a second timepoint. The pulse timing control unit 642 may receive data from temperature sensor 624, and may initiate the therapeutic laser pulse at a first timepoint based on, e.g., a manual signal from a user or a determination that target skin area has been cooled to a desired surface temperature (e.g., 15° C., 10° C., 5° C., 0° C., −5° C., −10° C., etc.). Pulse timing control unit 642 may also terminate the therapeutic laser pulse at a second timepoint based on, e.g., a predetermined pulsewidth or a determination that the surface temperature of the target skin area has reached a threshold surface temperature (e.g., indicating that a deeper target structure such as a sebaceous gland has reached a damage threshold temperature, e.g., 60° C.-75° C.).

Controller 640 also includes a temperature sensing control unit 644 that controls the operation of the TDU. Temperature sensing control unit 644 ensures that the TDU determines the surface temperature of a target skin area at a desired (e.g., programmed or predetermined) sampling rate such as 10 or more times per second. Controller 640 may synchronize the operations of the temperature sensing control unit 644 with the pulse timing control unit 642. In one embodiment, the pulse timing control unit 642 and the temperature sensing control unit 644 may comprise one or more of software, firmware, or other programming code operating in the controller 640. In one embodiment, the pulse timing control unit 642 and the temperature sensing control unit 644 may comprise separate processors or sub-processors, and/or separate executable code programs comprising one or more of software, firmware, etc., within controller 640. A wide variety of hardware and software designs may be used to achieve the functions described herein, and all are considered as within the scope of the present disclosure.

Controller 640 may also control other operations within the therapeutic laser treatment system 600 (e.g., software and firmware units and subunits, timers, mechanical or electrical elements or subsystems, etc.). These functions may also include, without limitation, control of the positioning of a movable scanning mirror for determining a target skin area, as discussed above and in greater detail in connection with FIGS. 7 and 9A-9F. Controller 640 also controls the operation of cooling system 622, including without limitation the temperature at which the cooling window is maintained (which may be determined by a user or by the patient's skin type as described in connection with FIG. 6B), the cooling capacity (i.e., the thermal energy removal rate of the TEC), status alarms, etc.

A user interface 650 is preferably provided to allow a system user to select or program one or more parameters (e.g., beam diameter or spot size, fluence, wavelength, target temperature of the surface of the target skin area, cooling temperature of the target skin area at which a pulse may be delivered, etc.) to control the operation of therapeutic laser system 600. User interface 650 may also display various status indicators and data associated with the system and/or a treatment session, such as the current laser parameters, duration of treatment, number of pulses delivered, etc. Controller 640 may also receive and process inputs from the user interface 650, and provide outputs to the user interface. In alternative embodiments, the user interface may be omitted.

Finally, the system 600 includes a power supply 660 for providing power to one or more of the foregoing portions of the system. In one embodiment, power supply 660 may comprise a power supply coupled to a standard NC power outlet to convert AC to DC power at one or more voltages, and may include a battery (e.g., for backup in the event of a power outage), a supercapacitor, etc. Power supply 660 also provides power to controller 640, which in turn includes a current-controlled power supply for driving the laser 610 and/or other system components and subassemblies at rapid switching rates based on inputs from pulse timing control unit 642, temperature sensing control unit 644, cooling system 622, temperature sensor 24, and scanner 634.

FIG. 6 illustrates a system according to certain embodiments of the invention involving cooling the skin before, during, or after pulse delivery. Alternative embodiments of the invention include systems with no cooling of the skin, or without cooling of the skin during one or more of the periods before, during, or after delivery of the therapeutic laser pulse. Additional alternative embodiments include systems in which different cooling capacities (i.e., rate of heat removal from the skin) are used in the periods before, during, or after delivery of the laser pulse, and during portions of these periods.

Figure 7A:
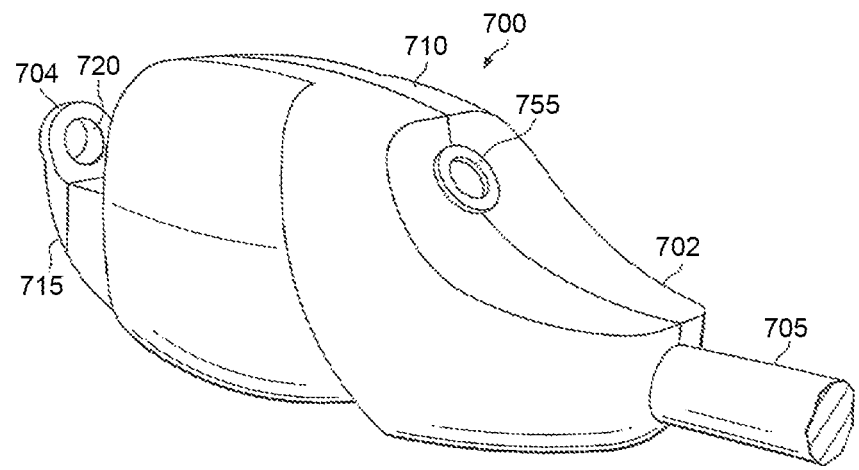
FIGS. 7A and 7B are perspective views of a handpiece according to an embodiment of the present invention.
Figure 7B:
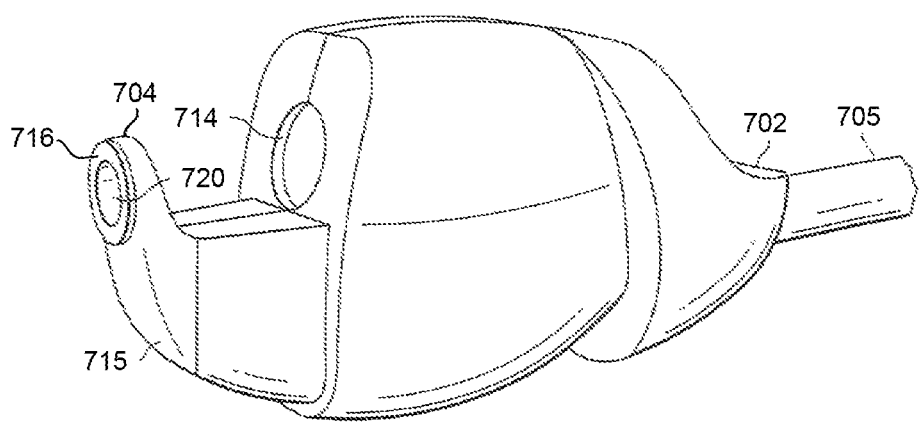

FIGS. 7A and 7B are perspective views, respectively, of one embodiment of a handpiece 700 for providing laser therapy to a patient's skin as part of a laser treatment system. The handpiece 700 provides contact cooling of the skin, at one or more timepoints before, during, or after application of therapeutic laser energy to the patient's skin.

Handpiece 700 includes a proximal end 702 and a distal end 704, and comprises a housing 710 having a shape adapted for holding by a user (e.g., a physician or technician), and having an inner volume shielding a plurality of optical elements. An optical cable 705, which comprises an optical fiber core (not shown), is coupled to the proximal end 702 of the handpiece 700. Optical cable 705 is coupled to a laser source (not shown) which generates and delivers laser pulses to the handpiece 900 through the cable. Optical cable 705, and specifically the optical fiber therein, terminates inside the proximal end 702 of handpiece 700 in a standard optical coupler (not shown) such as an SMA coupler, although other standard optical couplings may be used.

At the distal end 704 of the handpiece 700, a contact cooling unit 715 includes a cooling window 720 to cool, by direct contact, a first skin area equal in size to the cooling window. In addition to the cooling window 720, contact cooling unit 715 also comprises other optical elements, including a cooling window heatsink 716 that surrounds the cooling window 720 and a thermoelectric cooler (TEC) (not shown). Laser pulses from optical cable 705 pass through handpiece 700 along a first optical path and are applied to a target skin area, which comprises a smaller skin area within the first skin area cooled by the cooling window.

As shown in FIG. 7B, housing 710 of handpiece 700 includes an optical aperture or port 714 through which laser pulses exit the housing and travel along the first optical path through the cooling window 720 to the target skin area. Cooling window 720 is spaced a desired distance from housing 710 by cooling unit 715, which also functions as a spacing member to allow a user to visualize the area being cooled and treated by the handpiece 900.

As noted in the discussion of FIG. 6, in some embodiments a contact sensing element or system may be provided to ensure good contact between the skin of the patient and the cooling window during treatment. In various embodiments, contact may be sensed by electrical contacts (e.g., electrodes capable of sensing changes in electrical conductivity or resistivity of the skin), or by detecting other skin parameters associated with contact such as force, pressure, vibration, temperature, sweat, etc. In a particular embodiment, the invention comprises systems and methods for laser treatment using a handpiece capable of sensing one or more of contact, pressure, or force on the external periphery of the cooling window. By sensing the pressure or force between the contact sensor and the skin, the system can determine when contact between the skin and cooling window is sufficient to enable effective treatment to be achieved.

Poor contact may result in non-uniform cooling such that one or more target skin areas within the first skin area (i.e., the skin area in contact with the cooling window) are not cooled to a sufficiently low temperature to avoid pain, discomfort, or damage to overlying a target during laser pulse(s), especially for deeper target structures such as a sebaceous gland. Poor contact may involve a failure to fully contact the skin with the cooling window; failure to maintain even pressure of the cooling window across the first skin area; maintaining excessive pressure on the skin; or maintaining too little pressure. For example, if part of the cooling window is not in contact with the skin, or pressure is not evenly maintained, cooling may be uneven. Where cooling is uneven, some target skin areas may be overheated, while others may be underheated, resulting in poor efficacy. Additional details on contact, force, and pressure sensing may be found in related U.S. Provisional Application Ser. No. 63/125,354, filed Dec. 14, 2020, entitled "Dermatological Laser Systems and Methods with Pressure Sensing Handpiece," incorporated by reference herein in its entirety.

In alternative embodiments (not shown) a contact cooling unit may be omitted, and the handpiece may comprise a pulse delivery region to deliver the laser pulses through a pulse delivery aperture that does not comprise a contact cooling unit.

In preferred embodiments, a contact indicator may be provided, which may comprise a user interface similar to user interface 755 (FIG. 7A). The contact indicator may provide one of a contact feedback parameter, a force feedback parameter, and a pressure feedback parameter to a user.

The feedback parameter may indicate to a system user, based on contact, force, and/or pressure, one or more of the following feedback parameters: an indication of whether or not the handpiece (e.g., as confirmed by each of the plurality of contact sensing elements) is in contact with the patient's skin; an indication of the force exerted by the handpiece against the patient's skin; an indication of the pressure exerted by the handpiece against the patient's skin; an indication of one of the variation in pressure and the variation in force at one or more of the different locations of the contact sensing elements; an indication one of the variation in pressure and the variation in force between two or more of the contact sensing element locations; an indication that the pressure exerted by the handpiece against the skin exceeds a minimum pressure threshold; an indication that the pressure exerted by the handpiece against the skin is less than a maximum pressure threshold; an indication of the force at each of the different locations; an indication of the variation in force between two or more of the different locations; an indication that the force exerted by the handpiece against the skin exceeds a minimum force threshold; and an indication that the force exerted by the handpiece against the skin is less than a maximum force threshold.

FIGS. 8A-8D illustrate exemplary laser sources usable in laser treatment systems of the present invention (e.g., the system of FIG. 6) that, when coupled with a handpiece (e.g., the handpiece of FIGS. 7A and 7B) having one or both of a skin cooling system and a temperature determination unit (TDU), provides improved temperature control for treating tissues with poor chromophore selectivity. Each of the lasers incorporates a grating element to reduce the amplification of longitudinal modes outside of a desired center wavelength (e.g., a wavelength ranging from about 1725-1728 nm near the peak ratio of the absorption coefficients of sebum and water, such as about 1725.5, 1726, 1726.5, 1727, or 1727.5 nm). Use of such a laser helps ensure that substantially all of the available laser energy is within a desired tolerance value of the wavelength having the maximum absorption coefficient ratio of sebum to water, which helps to reduce discomfort associated with applying laser pulses to sebaceous gland tissue. When used in a system that also provides contact cooling of the skin, the laser sources illustrated in FIGS. 8A-8D can reduce laser energy absorbed by non-target tissues above a sebaceous gland.

Figure 8A:
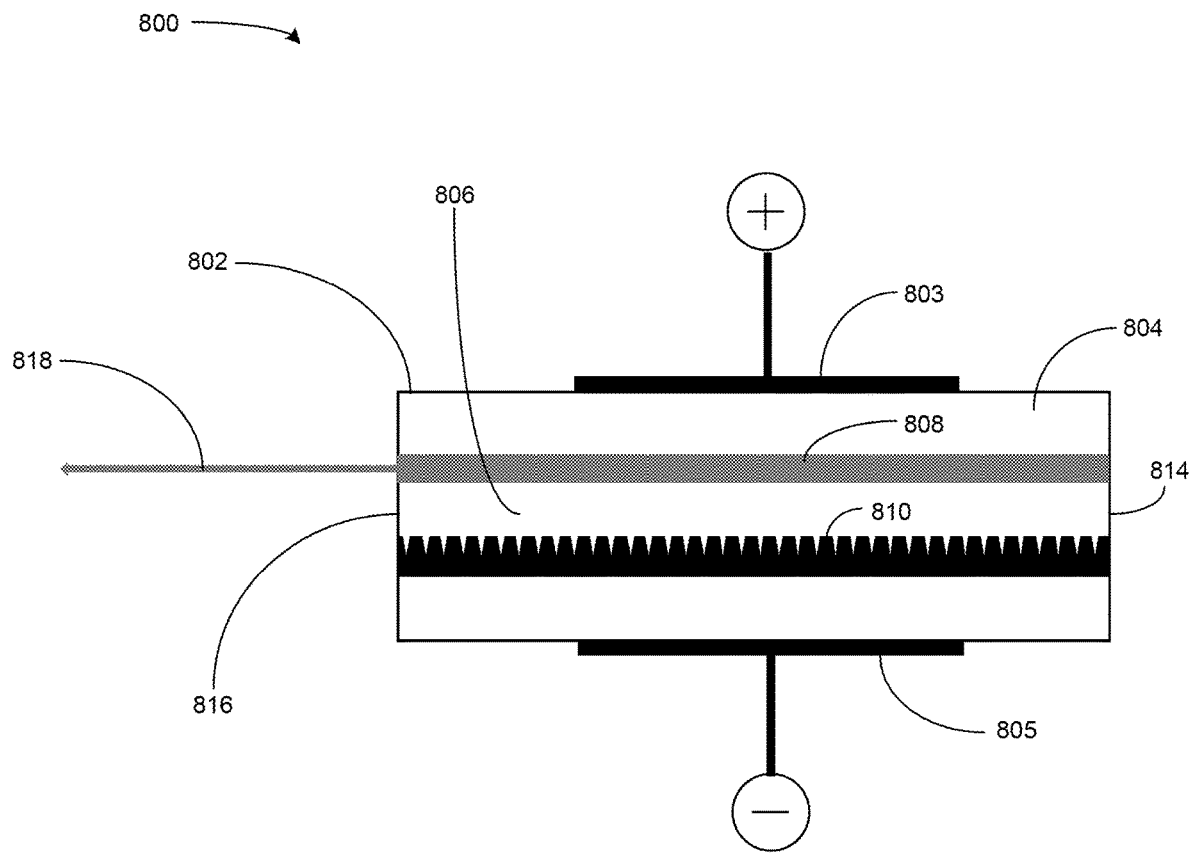
FIGS. 8A-8D are optical schematics of laser sources used in certain embodiments of the invention.

FIG. 8A illustrates a distributed feedback (DFB) laser 800, which provides a continuous Bragg grating reflector 810 disposed along (and generally parallel to) the entire gain medium 808 of the laser.

If sufficient gain is present within gain medium 808, no additional outcoupling mirror is required for the DFB laser, and the continuous Bragg grating reflector 810 is responsible for all optical feedback to dampen out undesired modes during generation of laser light, resulting in laser emission having a narrow linewidth that is less than half of the linewidth that would be present in the absence of the continuous Bragg grating reflector element 810. In one embodiment, the gain medium 808 is such that it would have a linewidth of 1000 GHz or more in the absence of the continuous Bragg grating reflector element 810, and the Bragg reflector is selected and incorporated into substrate 802 so as to reduce the linewidth of the emitted light 818 to 500 GHz or less, and preferably 300 GHz or less. The frequency selection of the continuous Bragg grating reflector 810 may be much narrower than that provided by a broad band mirror and as such a DFB laser will operate in a single longitudinal mode.

Figure 8B:
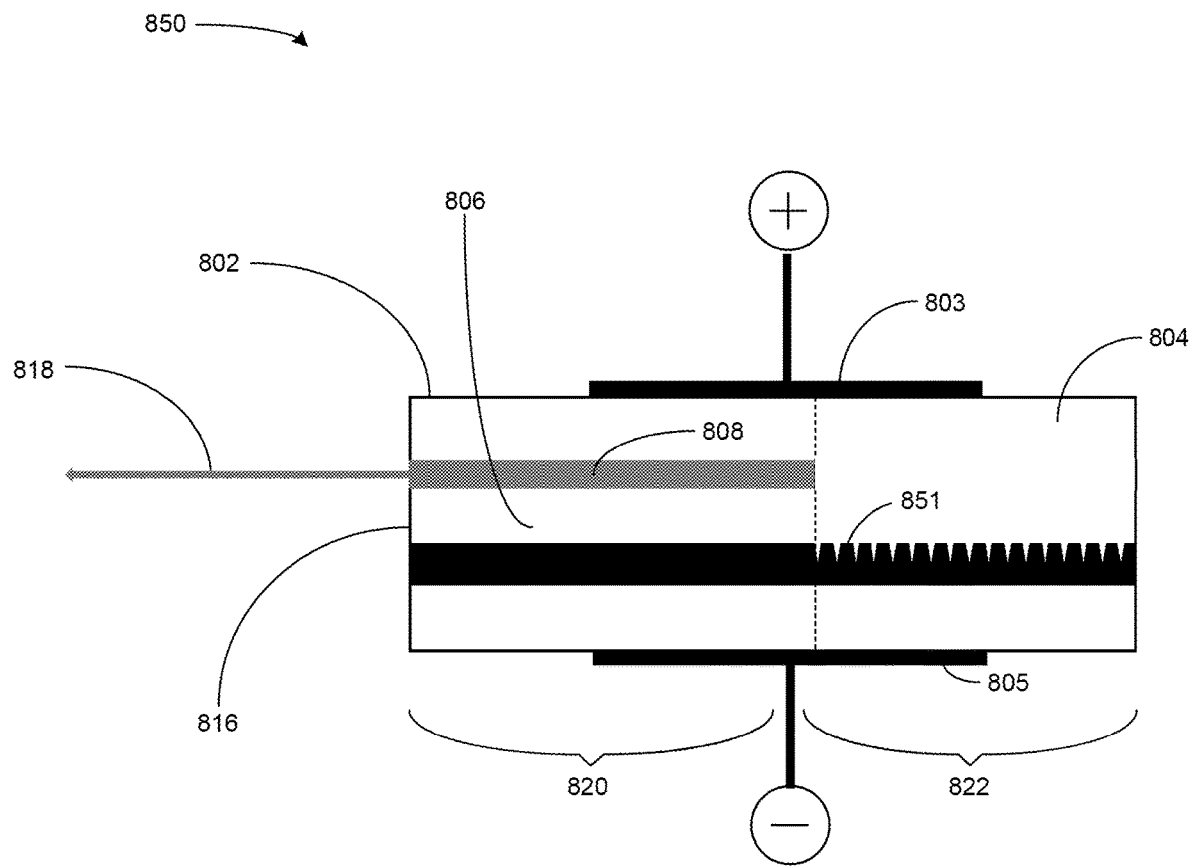

FIG. 8B illustrates a distributed Bragg reflector (DBR) laser 850, which may also be used in embodiments of the present disclosure to reduce the linewidth of the laser light applied to the patient's skin. The DBR laser includes many of the elements of the DFB laser 800 of FIG. 8A, and like numerals are used to refer to like structures in FIG. 8B. However, in DBR laser 850, the fully reflective mirror 814 of FIG. 8A is replaced by a distributed Bragg grating 851 along the longitudinal direction (i.e., generally parallel to gain medium 808) and outside of the gain region characterized by the presence of gain medium 808. Such a distributed continuous grating reflector tends to reflect a narrower band of wavelengths, increasing the wavelength stability of the diode laser.

Referring again to FIG. 8B, DBR laser 850 includes a gain region 820 in which the gain medium 808 is pumped to generate laser light, and a feedback region 822 coupled to the gain region that provides feedback to reduce the amplification of undesired modes of laser light in the gain region. DBR laser 850 also includes a semiconductor substrate 802 that includes the gain medium 808, which may be pumped by an electrode pair (e.g., anode 803 and cathode 805) to produce laser light. Substrate 802 may be fabricated in layers using known processes, and may include a p-type layer 804, an n-type layer 806, or additional layers (not shown). DBR laser 850 includes a partially reflective mirror 816 at one end, and laser light emitted from the mirror may be directed to skin tissue of a patient via a handpiece coupled to the DBR laser. As previously noted, fully reflective mirror 814 (FIG. 8A) is replaced by distributed Bragg grating reflector element 851 disposed in a feedback region 822 that is outside—but optically coupled to—the gain region 820. Distributed Bragg grating reflector element 851 is selected to reflect back into the gain region 820 a desired mode (e.g., a first order mode) of laser light, which results in amplification by the gain medium 808 of the selected wavelength reflected by the distributed Bragg grating 851 and the suppression of all other wavelengths.

The net result, with proper selection of distributed Bragg grating reflector 851, is an optical feedback from the distributed Bragg grating that dampens out undesired modes of laser light in the gain region 820, and a narrow linewidth of the output light 818 that is less than half of the linewidth that would be present in the absence of the distributed Bragg grating reflector element. In one embodiment, the gain medium 808 is such that it would have a linewidth of 1000 GHz or more in the absence of the continuous Bragg grating reflector element 851, and the Bragg reflector is selected and coupled to the gain medium 808 so as to reduce the linewidth of the emitted light 818 to 500 GHz or less, preferably 300 GHz or less, and more preferably 200 GHz or less.

Figure 8C:
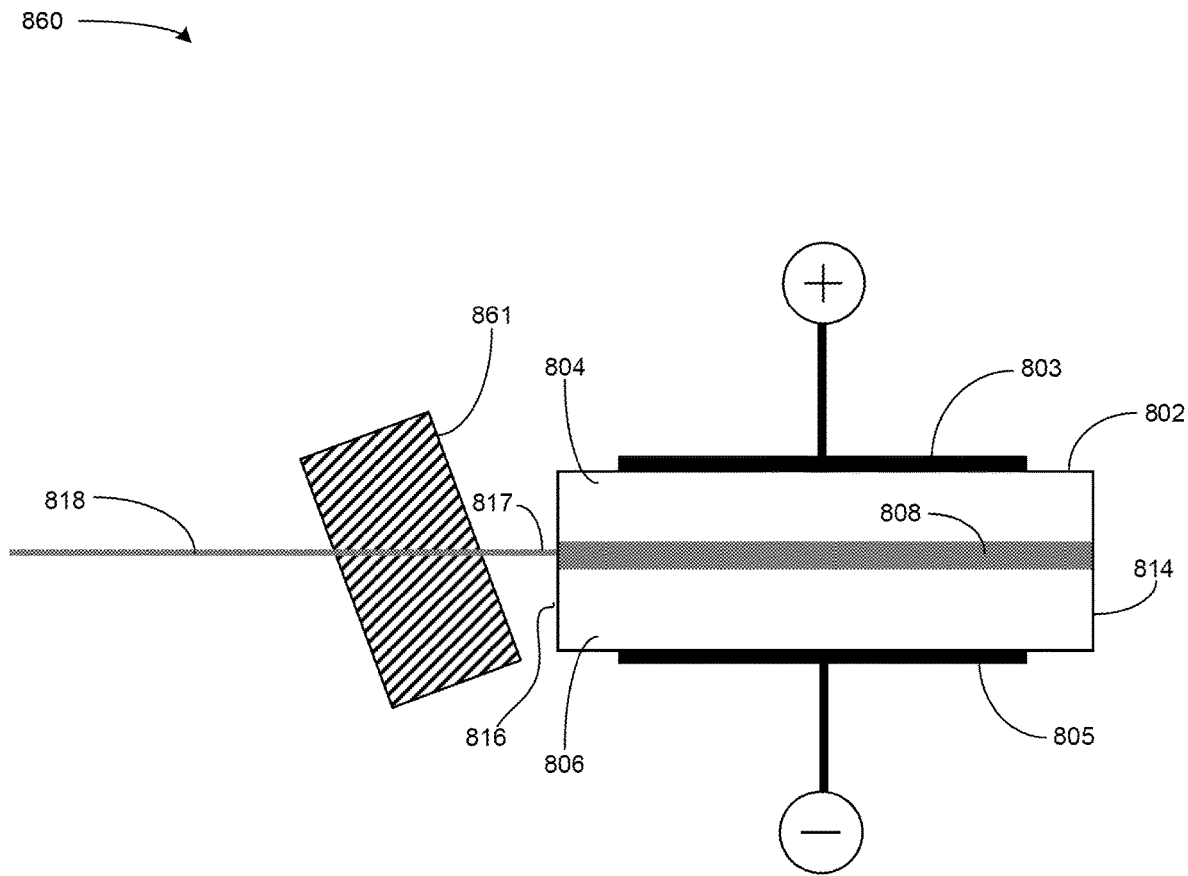

FIG. 8C illustrates a volume holographic grating (VHG) laser system 860 that may be used in embodiments of the present disclosure. In the embodiment of FIG. 8C, a volume holographic grating Bragg reflector is located externally to a semiconductor laser substrate 802 and optically coupled thereto to dampen out undesired modes. In particular, a VHG Bragg grating 861 is placed as a separate element in front of the diode laser. This implementation has the advantage of thermally decoupling the reflector from the diode laser itself, further improving thermal wavelength stability.

In the VHG system 860, a semiconductor laser substrate 802 includes a gain medium 808 pumped by an electrode pair (803, 805) to produce laser light. Substrate 802 may include a p-type layer 804, an n-type layer 806, or additional layers (not shown). Laser substrate 802 further includes a fully reflective mirror 814 at one end and partially reflective mirror 816 at another end. Laser light 817 emitted from partially reflected mirror 816 exits the semiconductor laser substate 802 and engages volume holographic grating (VHG) Bragg element 861, which reflects a portion of the light back along path 817, and transmits a portion of the light 818 for application to the skin of the patient via a handpiece coupled to the VHG laser system 860.

While the distributed Bragg grating reflector element 851 of FIG. 8B is located outside the gain region but within the semiconductor laser substrate 802, the VHG Bragg element 861 of FIG. 8C is located entirely outside of the diode laser substrate 802. In addition to thermally decoupling the VHG Bragg element from the diode laser substrate 802 as noted above, the VHG Bragg element is selected to reflect back into the gain medium 808 a desired mode (e.g., a first order mode) of laser light 817 received from the substrate via mirror 816. Like the distributed Bragg grating 851 of FIG. 8B, VHG Bragg element 861 results in a feedback amplification of a selected wavelength reflected back into the gain medium 808 from the VHG, and the suppression of all other wavelengths.

By selecting the VHG Bragg element 861 to provide a feedback amplification of only a desired mode, undesired modes of laser light in the gain medium 808 are eliminated, and the output light 818 has a linewidth that is less than half of the linewidth that would be present in the absence of the VHG Bragg element 861. In one embodiment, gain medium 808 would have a linewidth of 1000 GHz or more in the absence of the VHG 861, and the VHG is selected and coupled to the gain medium 808 so as to reduce the linewidth of the emitted light 818 to 500 GHz or less, and preferably 300 GHz or less.

Figure 8D:
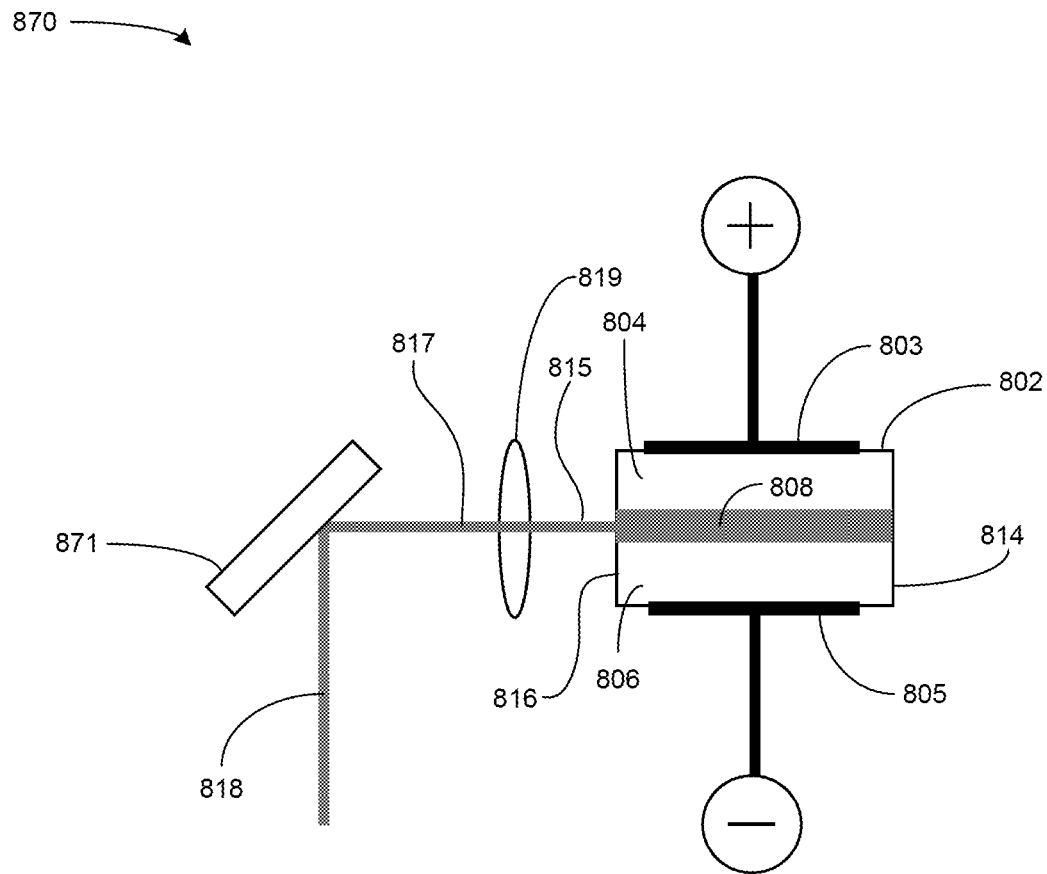

FIG. 8D illustrates an external cavity diode laser (ECDL) system 870. In an ECDL, the output light 815 from a gain medium 808 of a diode laser substrate 802 is first collimated by a lens 819 (or other optical elements), and then sent along path 817 onto an external cavity diode laser (ECDL) Bragg grating 871 which reflects a narrow longitudinal mode back into the diode laser along path 817, through collimating lens 819, and the path taken by the output light 815 from the diode laser. Due to the typically larger cavity length in the ECDL configuration 870, extremely narrow linewidths of <1 MHz can be achieved.

The ECDL system 870 functions similarly to VHG system 860, in that the grating element 871 (or 861 in the VHG system) is located entirely outside the semiconductor laser substrate 802. Referring to FIG. 8D, the ECDL diode laser substrate 802 includes a gain medium 808 pumped by an electrode pair (803, 805) to produce laser light, and may include a p-type layer 804, an n-type layer 806, or additional layers. A fully reflective mirror 814 is provided at one end of the substrate 802, and partially reflective mirror 816 is provided at the other end. Laser light 815 is emitted from partially reflected mirror 816 and passes through collimating optics 819 (e.g., a lens) before engaging the ECDL Bragg grating 871, which is selected to reflect a desired mode of the light back along path 817, and to transmit a portion of the light 818 for application to the skin of the patient via a handpiece coupled to the ECDL system 870.

Because it is positioned entirely outside the diode laser substrate 802, the ECDL grating 871 is thermally decoupled from the substrate, and by reflecting back a desired mode into the gain medium 808, ECDL Bragg grating 871 results in a feedback amplification of a selected wavelength and the suppression of all other wavelengths.

As with the VHG 861, ECDL Bragg grating 871 is selected to provide a feedback amplification of only a desired mode, eliminating undesired wavelengths of light in the gain medium 808, and resulting in output light 818 having a linewidth that is less than half of the linewidth that would be present in the absence of ECDL Bragg grating 871. In one embodiment, gain medium 808 would have a linewidth of 1000 GHz or more in the absence of the ECDL Bragg grating 871, and the ECDK Bragg grating is selected and coupled to the gain medium 808 so as to reduce the linewidth of the emitted light 818 to 500 GHz or less, and preferably 300 GHz or less.

Laser sources as shown in FIGS. 8A-8D have not been utilized in dermatological applications because it has been thought that the increase in complexity of such systems, and the added expense, fabrication time, and failure modes exceed any benefit from their use. Moreover, instances of poor chromophore selectivity can in some cases be avoided by simply selecting a different wavelength for which the target chromophore has relatively good selectivity over a non-target chromophore. Consequently, instances of poor chromophore selectivity such as discussed in connection with the treatment of acne have been largely dismissed. Moreover, solid-state lasers can typically provide sufficient power to heat target structures in a much narrower timeframe, which is advantageous for small target structures with short TRTs. However, such lasers are only available for a small selection of wavelengths.

Figure 9:
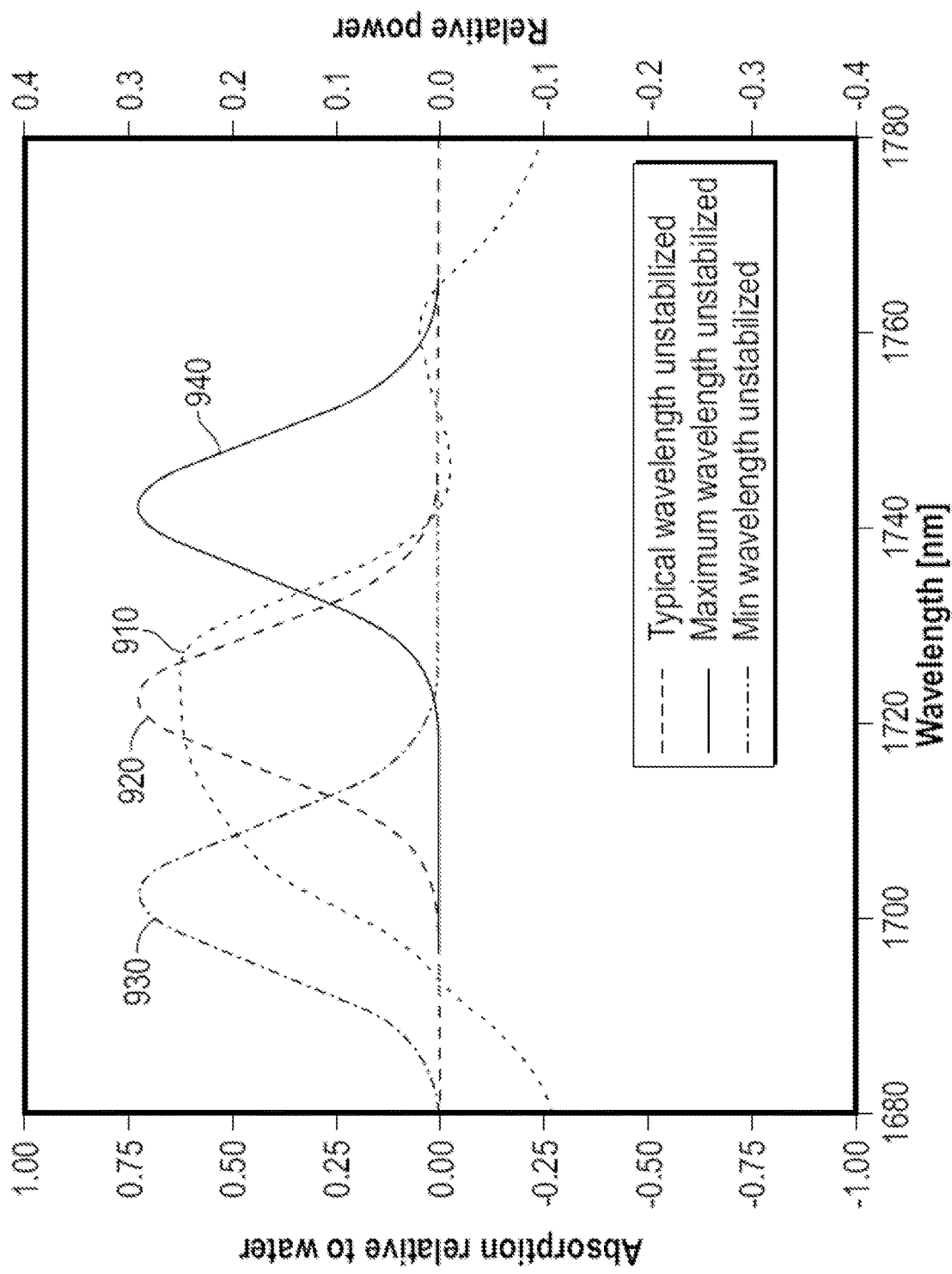
FIG. 9 is a graph showing wavelengths for which sebum absorption is higher than the absorption in water for three representative lasers exemplary of the prior art.
Figure 10:
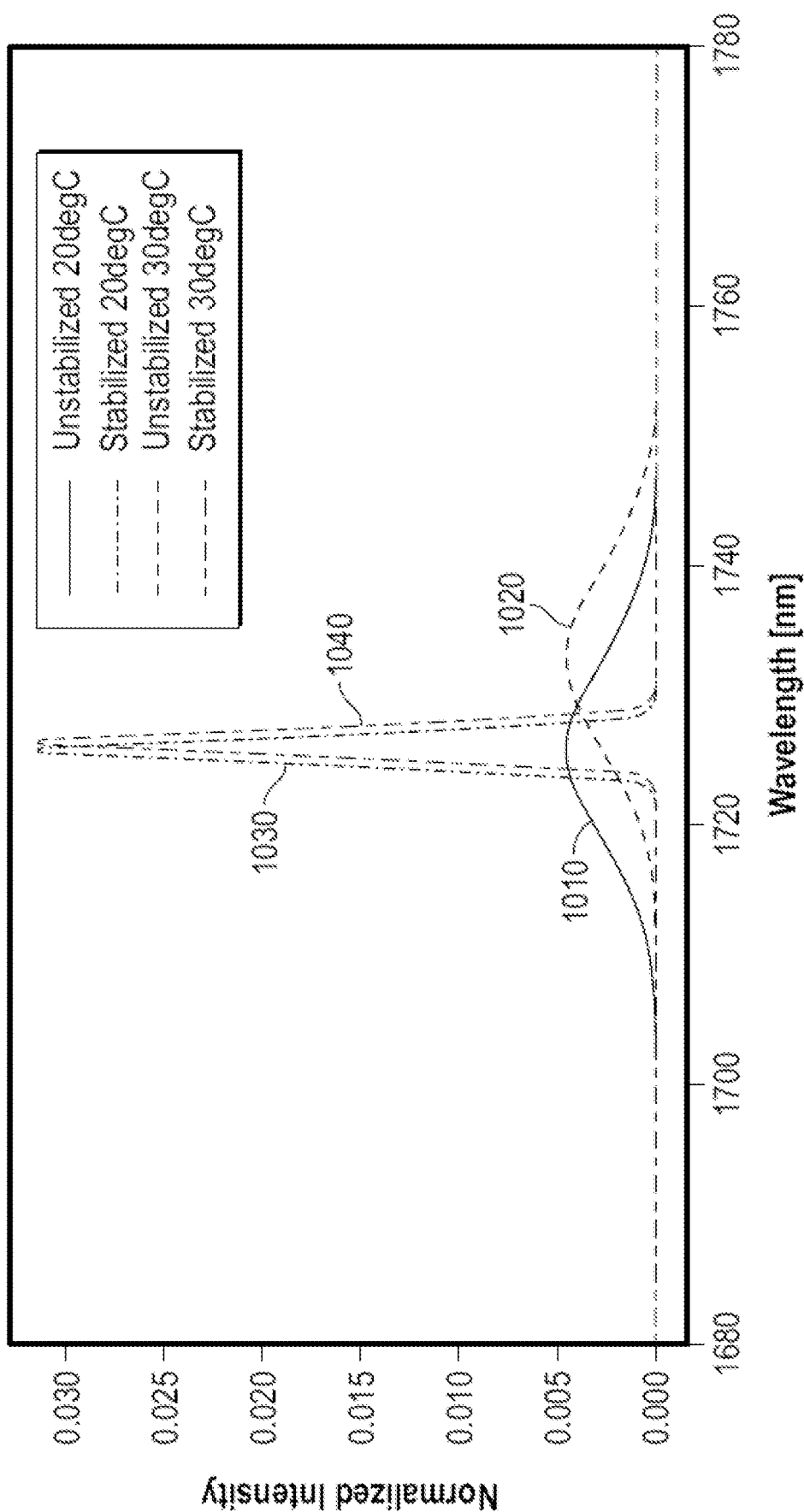
FIG. 10 is a graph comparing the wavelength stability of an embodiment of the present invention to the prior art.
Figure 11:
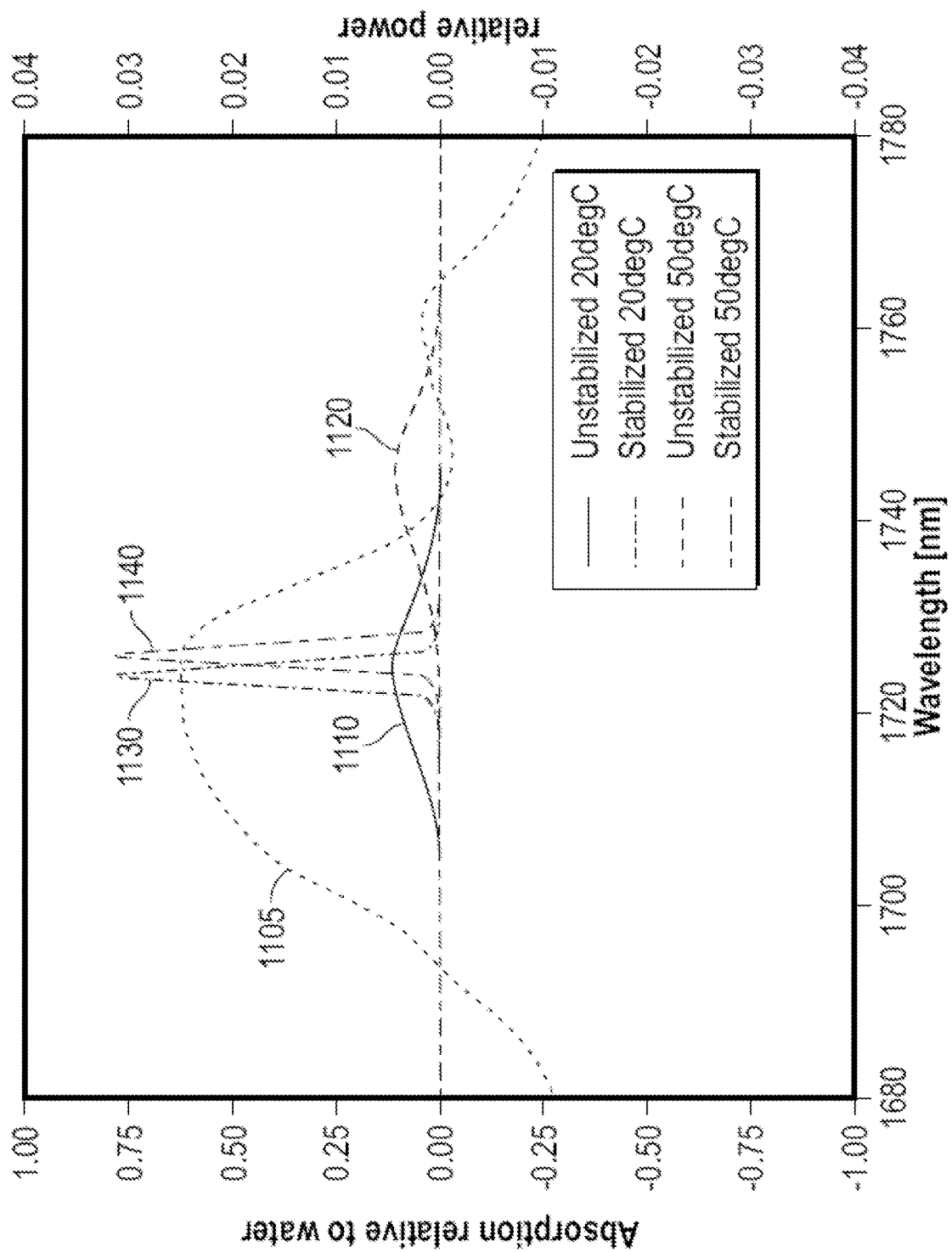
FIG. 11 is a graph illustrating the improvement of wavelength stability for treatment of sebum tissue in an embodiment of the present invention.

FIGS. 9-11 are graphs illustrating the improved control of heating sebum tissue using systems of the present disclosure. FIG. 9 is a graph showing wavelengths for which sebum absorption is higher compared to the absorption in water (curve 910), displayed on the left-hand side y-axis as the ratio of the absorption coefficients of sebum and water. A value of curve 910 above 0 shows preferential absorption in sebum compared to the water. The three gaussian profiles 920, 930, 940 are abstracted output spectra of three typical unstabilized diode lasers used in prior art systems, with a target wavelength of 1725 nm. A typical unstabilized diode laser as used in prior art approaches has multiple effects influencing its center wavelength and linewidth. The width of the gaussian profile as a whole (i.e., from the left side of curve 930 to the right side of curve 940), incorporating all three gaussian provides, illustrates the expected linewidth of an unstabilized diode laser for one center frequency with manufacturing variances taken into account. During manufacturing, the center wavelength of a diode laser varies from unit to unit within a certain wavelength range. The two outer gaussian spectral profiles illustrate the expected upper and lower ranges in a typical manufacturing environment. While the diode laser 920 that is in the center of the range matches the absorption profile of the sebaceous gland for the wavelength range with maximal preferred absorption (having a center wavelength peak at just over 1720 nm), it will be noted that both of the other curves 930, 940 represent lasers that would typically be received from a manufacturer, but which would provide poor performance, as indicated by the negative absorption values for the ends of curve 910— indicating that water would more strongly absorb light at those wavelengths than sebum, resulting in overtreatment and pain of the tissue above the sebaceous gland, and likely undertreatment of the sebaceous gland.

FIG. 10 is a graph illustrating the improvement in wavelength stabilization and control of thermal damage to tissue for systems of the present invention compared to prior art systems at wavelengths discussed in connection with FIG. 3 regarding the region of poor chromophore selectivity for sebum compared to water (e.g., about 1700-1740 nm). FIG. 10 shows that thermal effects of lasers contribute to wavelength instability. Curves 1010 and 1020 demonstrate how the output of an example prior art laser (e.g., without grating stabilization of wavelength as disclosed herein) would shift if the operational conditions changed from 20° C. to 30° C. These curves illustrate the need for controlling the laser operating temperature, which can be challenging. A change in operating temperature of 10° C. can easily result in a shift of 7 nm in the output wavelength, which could result in a significant increase in pain to the patient, undertreatment of the target chromophore (sebum) and overtreatment (e.g., burning) of the overlying tissue, for which water is the dominant chromophore. Especially in pulsed operation, the temperature of the laser diodes can easily change by 20-40° C. when switched on, adding additional difficulty to controlling the output spectrum of the laser.

Curves 1030 and 1040 illustrate the narrowing of the linewidth that is expected when designing a laser with the same target center wavelength in a system using a distributed feedback (DFB) laser source (e.g., the laser of FIG. 8A) to narrow the linewidth of laser pulses in the treatment of tissues at wavelengths of about 1725-1728 nm. The linewidth—illustrated by the width of curves 1030 and 1040—is significantly narrower than that of curves 1010 and 1020 of prior art lasers with unstabilized wavelengths. Without being bound by theory, it is believed that a linewidth reduction of about a factor of 10 can typically achieved using embodiments of the present invention. FIG. 10 also illustrates the reduction of the wavelength change caused by a temperature shift of a DFB laser. Curves 1030 and 1040 show that a shift in the output wavelength of systems according to the present disclosure limited to about 1-2 nm can be achieved despite an operating temperature change from 20° C. to 30° C. In the example of FIG. 10, a reduction in wavelength shift by a factor of 6 is achieved compared to the prior art systems. The increased temperature stability directly translates into less spectral (wavelength) shift during pulsed operation of the laser. The laser diodes still heat up by a significant amount, but the resultant shift of the output spectrum is significantly reduced.

Accordingly, in some embodiments of the present invention, a cooling system is provided to cool a grating-stabilized laser source to minimize the thermal wavelength shifts occurring as the laser heats up during operation. In one embodiment, the cooling system comprises a thermoelectric cooler (TEC) coupled to a baseplate to which the laser modules are mounted. In one embodiment, the cooling system comprises circulating water through channels in the baseplate.

FIG. 11 is a graph overlaying the output spectrum of idealized diode laser modules according to both the prior art (curves 1110 and 1120) and embodiments of the present disclosure (curves 1130 and 1140) with the absorption spectrum of sebum relative to water (curve 1105). Ideally, the output spectrum of the laser should overlap with the absorption spectrum in the region of the maximum absorption coefficient ratio to preferentially heat the sebum instead of the surrounding tissue. When creating a train of multiple pulses of therapeutic fluence, the accumulation of thermal energy inside the diode lasers results in a temperature increase of the laser diodes of roughly 30° C. As shown in FIG. 11, even for a perfectly selected diode laser of the prior art (curves 1110 and 1120) this temperature change will result in a shift of the output spectrum of the laser into a region for which the laser light is more strongly absorbed by water rather than sebum, meaning that the system fails to provide laser energy in the desired range to treat acne and causing significant pain, overtreatment of tissue overlying the sebaceous gland, and undertreatment of the sebum tissue. This would translate into a larger temperature rise in the tissue above the sebaceous gland rather than the gland itself, and as a result the damage to the overlying tissue would be greater than the damage to the sebaceous gland. This effect can be mitigated by limiting the number of consecutive pulses to limit the increase in the temperature rise of the laser (reducing the amount of the shift), or by firing the laser into a beam dump before directing the laser onto the target tissue. Both options, however, require a more complex design. In addition to the described thermal effect, manufacturing variation between diode laser modules (e.g., as discussed in FIG. 9) can result in an additional shift of the center wavelength of +/−20 nm which would necessitate additional controls or lower yield as the output spectrum might further shift outside of the wavelength range of preferential absorption by sebum.

FIG. 11 further illustrates that, for a DFB laser according to one embodiment of the present disclosure (curves 1130 and 1140), the reduction in spectral shift with temperature results in an output spectrum that is still favorably absorbed by the sebum even after a 30° C. temperature increase of the laser. Consequently, the output spectrum still results in a preferential heating of the sebaceous gland compared to overlying tissue comprising water as the primary chromophore, even after a long pulse train.

Figure 12A:
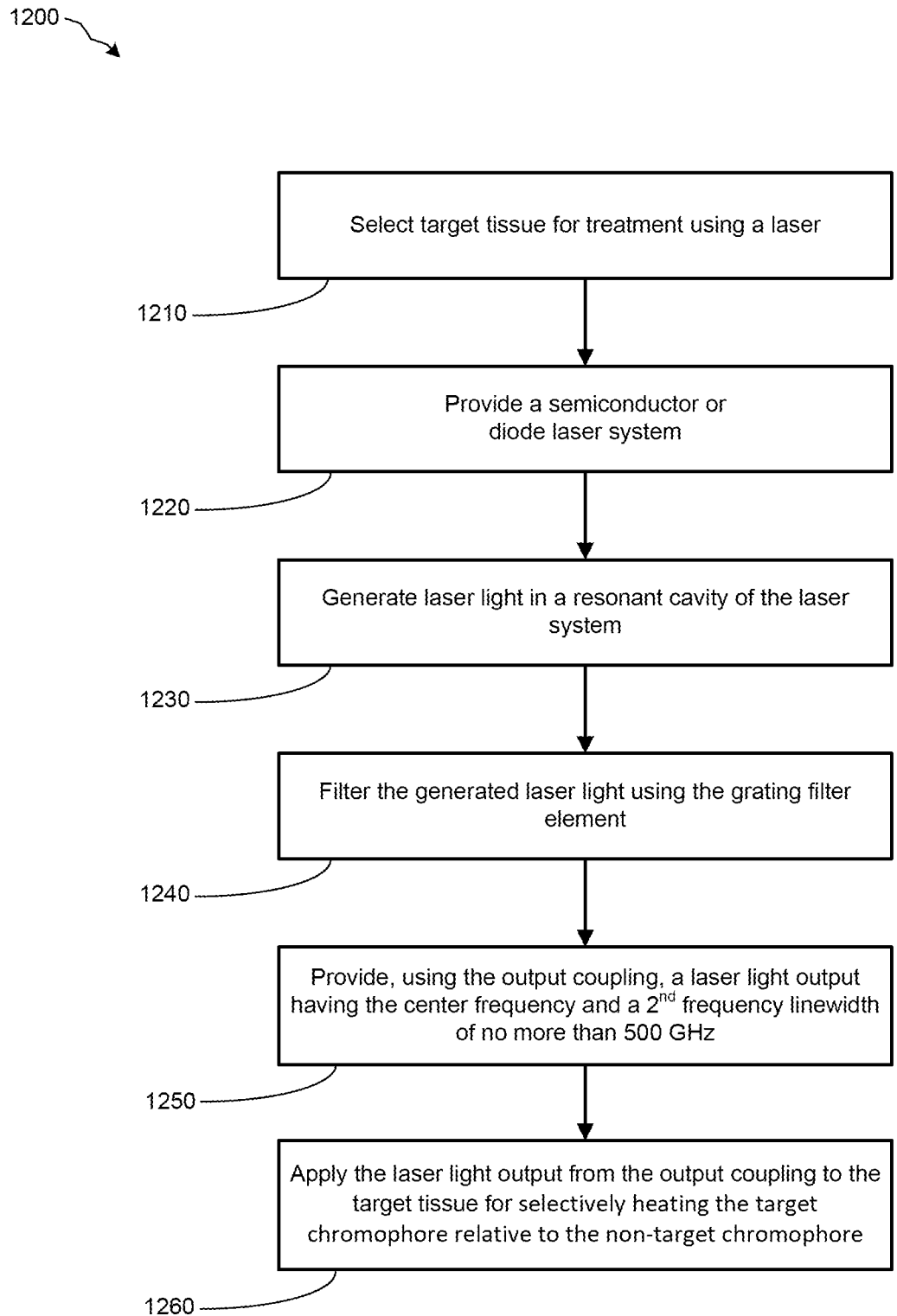
FIG. 12A is a flowchart depiction of a method for treating a patient using a laser, according to an embodiment of the invention.
Figure 12B:
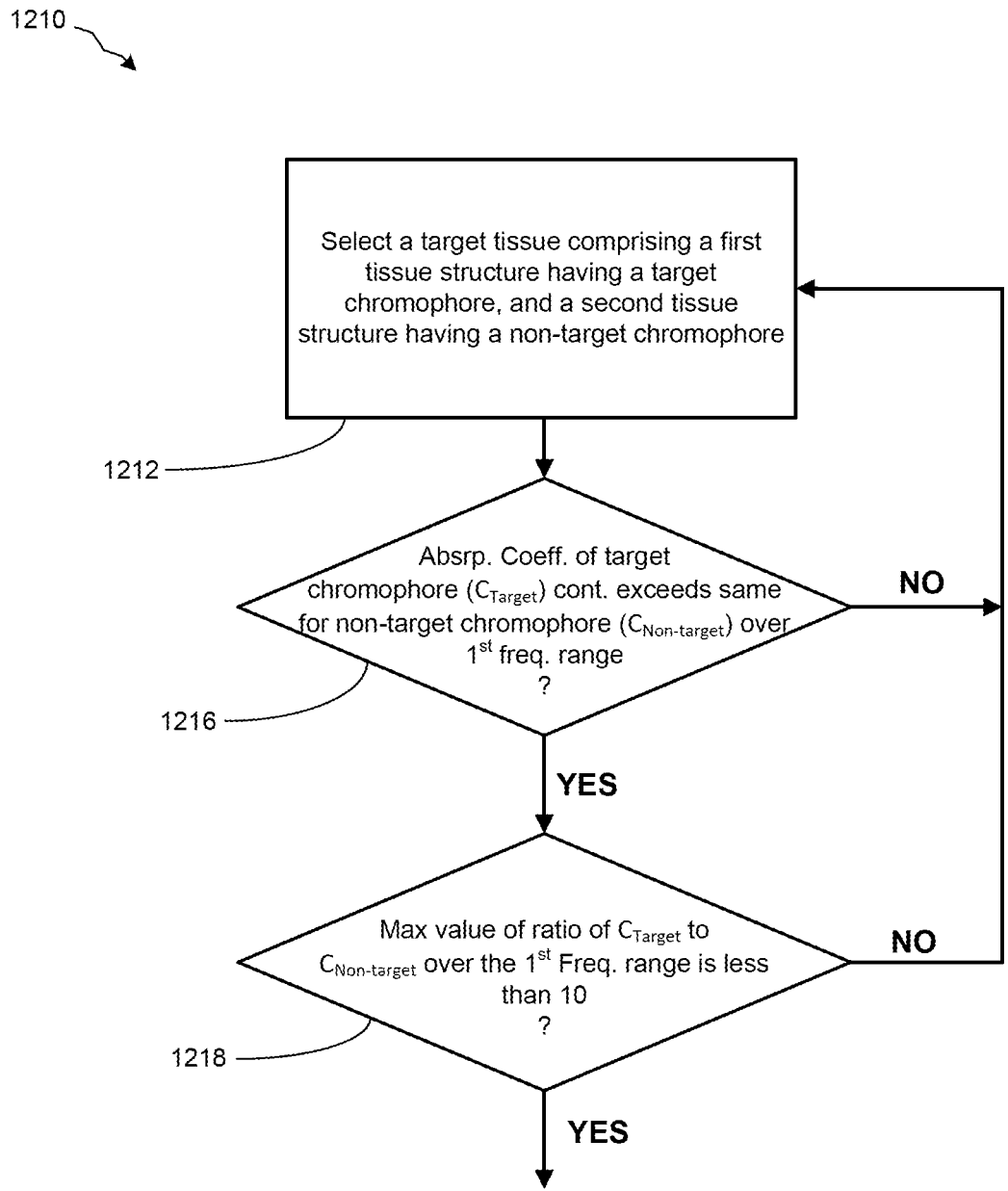
FIG. 12B is a flowchart depiction of a more detailed description for selecting the target tissue of the patient for providing a treatment, according to an embodiment of the invention.

FIG. 12A illustrates a flowchart depiction of a method for treating a patient using a laser, in accordance with embodiments herein. A target tissue of a patient to be treated using a laser is selected (1210). FIG. 12B illustrates a flowchart depiction of a more detailed description for selecting the target tissue of the patient to be treated, in accordance with embodiments herein.

Turning now to FIG. 12B, the target tissue to be treated includes a first tissue structure that has a target chromophore as well as a second tissue structure having a non-target chromophore (1212). That is, the target tissue includes both a structure having a target chromophore to be thermally damaged by absorption of laser light, and a structure having a non-target chromophore for which absorption of light is not intended or desired. FIG. 12B also illustrates that the target tissue has poor chromophore selectivity, as indicated at 1216 and 1218. In particular, the absorption coefficient of the target chromophore ($C_{Target}$) exceeds the absorption coefficient of the non-target chromophore ($C_{Non-Target}$) over a first frequency range from which a laser wavelength may be selected (1216). However, while the target chromophore has higher absorption than the non-target chromophore over the first laser frequency (or wavelength) range, it does not substantially exceed that of the non-target chromophore so as to enable thermal damage to the target chromophore structure while providing little or no damage to the non-target chromophore. In particular, the maximum value of the ratio of $C_{Target}$ to $C_{Non-Target}$ is less than 10 over the entire first frequency range. Thus, the target chromophore does not, for any laser frequency within the first frequency range, absorb 10 times or more of the energy compared to the non-target chromophore (1218). Only when both conditions 1216 and 1218 are satisfied is the target tissue structure considered one having poor chromophore selectivity, to which the embodiment of FIGS. 12A-12C is directed.

Returning to FIG. 12A, upon selecting a target tissue having poor chromophore selectivity for providing treatment, a laser, such as a semiconductor or diode laser is provided (1220). FIG. 12C illustrates a flowchart depiction of a more detailed description for providing a laser comprising a semiconductor or a diode laser system, in accordance with embodiments herein.

In FIG. 12C, a laser system is provided, wherein the laser system includes a laser gain medium that, in the absence of a grating filter element, is adapted to provide laser light having a center frequency within the first frequency range and a first frequency linewidth of at least 1000 GHz (1222). Providing the laser system also includes using a grating filter element that is capable of providing feedback to the light in the laser gain medium, and also capable of reducing the first frequency linewidth to a second frequency linewidth that is no more than half of the first frequency linewidth (1224). Further, using the laser system also includes using a system that includes an output coupling capable of providing a predetermined fraction of light from the laser gain medium (1226). The method then continues to block 1230 of FIG. 12A

Returning to FIG. 12A, upon providing a laser (1220), a laser light is generated in a resonant cavity of the laser system (1230). The generated laser light may then be filtered using the grating filter element (described in block 1224 of FIG. 12C) of the laser system (1240). Using the output coupling (described in block 1226 of FIG. 12C), a laser light output is provided (1250). In some embodiments, the laser light output may have a center frequency and a second frequency linewidth of no more than 500 GHz.

The laser light output may be applied to the target tissue (1260). This application enables the selective heating of the target chromophore to be performed, relative to the non-target chromophore. As such, treatment of the first tissue structure having the target chromophore may be heated to the maximum extent relative to the second tissue structure having the non-target chromophore.

In some embodiments, the system may also include a safety interlock preventing the laser source from generating the therapeutic laser pulse unless a desired force and/or pressure feedback parameter is provided by the contact indicator. In addition to the foregoing feedback parameters, the safety interlock may prevent the laser source from operating unless one of the following is provided: an indication that the pressure difference between the highest and lowest pressures among the different locations is less than a maximum pressure difference threshold, an indication that the difference between the highest and lowest applied forces among the different locations is less than a maximum force difference threshold; and an indication that desired cooling time has elapsed; and indication that a laser pulse has not exceeded a maximum pulse duration.

In various embodiments, the present invention relates to the subject matter of the following numbered paragraphs.

201. A system for treating a target tissue having poor chromophore selectivity, the target tissue comprising a first tissue structure comprising a target chromophore and a second tissue structure comprising a non-target chromophore, wherein the absorption coefficient of the target chromophore continuously exceeds the absorption coefficient of the at least one non-target chromophore over a first frequency range of less than 6000 GHz, and the maximum value of the ratio of the absorption coefficient of the target chromophore to the absorption coefficient of the non-target chromophore over the first frequency range is less than 10, the system comprising:
  a) a diode laser system having at least one semiconductor laser generating pulsed laser light, the at least one semiconductor laser comprising:
    1) a semiconductor laser gain medium that, in the absence of a grating filter element, produces laser light having a center frequency within the first frequency range and a first frequency linewidth of at least 1000 GHz;
    2) a grating filter element capable of providing feedback to the light in the laser gain medium, wherein the grating element is adapted to reduce the first frequency linewidth to a second frequency linewidth that is no more than one-half of the first frequency linewidth; and
    3) an output coupling adapted to output a desired fraction of light from the semiconductor laser gain medium as laser pulses;
  b) a handpiece to receive the laser pulses output from the diode laser system and to direct the laser pulses to the target tissue along a first optical path, the handpiece comprising:
    1) an optical connector to receive the laser light output from the output coupling of the diode laser system;
    2) a contact cooling element comprising a cooling window adapted to contact and cool a first skin area of the patient, wherein the cooling window comprises a thermally conductive material and wherein the target tissue comprises a volume of tissue having an external skin surface within the first skin area; and
    3) at least one optical element located in the first optical path and adapted to direct the laser light along the first optical path from the optical connector through the cooling window into the target tissue; and
  c) a temperature determination unit that determines a surface temperature of the target tissue one or more times before, during, or after the application of each laser pulse.

202. The system of numbered paragraph 201, wherein the cooling window comprises a thermally conductive material that is transmissive to infrared energy, and the temperature determination unit determines a surface temperature of the target tissue based on infrared energy radiated from the target tissue through the cooling window along a second optical path.

203. The system of claim 202, wherein the handpiece comprises at least one reflective optical element located in the second optical path, and wherein the temperature determination unit comprises:
  1) a temperature sensing element for sensing infrared energy radiated from substantially only the target tissue through the cooling window along the second optical path, the temperature sensing element generating a first signal indicative of the infrared energy radiating along the second optical path, wherein the infrared energy radiating along the second optical path engages the at least one reflective optical element before being directed onto the temperature sensing element; and
  2) a processor adapted to determine the surface temperature of the target tissue one or more times during or after the application of each therapeutic laser pulse based on the first signal.

204. The system of claim 201, wherein the diode laser system further comprises:
  4) a cooling system that cools the at least one semiconductor laser to maintain the at least one semiconductor laser at a temperature that varies by no more than 40° C. during operation of the at least one semiconductor laser to generate laser pulses for application to the target tissue.

205. The system of claim 204, wherein the cooling system is a dynamic cooling system that adjusts the cooling capacity based on the power applied to the at least one semiconductor laser.

206. The system of claim 204, wherein the cooling system comprises
  A) a thermoelectrical cooler; and
  B) a heat sink comprising a base plate thermally coupled to the thermoelectric cooler and to the at least one semiconductor laser, wherein the thermoelectric cooler controls the temperature of the base plate to a desired temperature within the range of 10-40° C. during the operation of the at least one semiconductor laser to generate laser pulses for application to the target tissue.

207. The system of claim 201, wherein the grating filter element provides feedback to the light in the laser gain medium to reduce the first frequency linewidth to a second frequency linewidth that is no more than 25% of the first frequency linewidth.

208. The system of claim 201, wherein the grating filter element provides feedback to the light in the laser gain medium to reduce the first frequency linewidth to a second frequency linewidth that is no more than 300 GHz.

209. The system of claim 201, wherein the grating filter element provides feedback to the light in the laser gain medium to reduce the first frequency linewidth to a second frequency linewidth for which at least 75% of the energy of the laser pulses is at a frequency for which the ratio of the absorption coefficient of the target chromophore to the non-target chromophore is at least 90% of the maximum value of the absorption coefficient ratio over the first frequency range.

210. The system of claim 201, wherein the diode laser system comprises a plurality of semiconductor lasers, each laser in the plurality of semiconductor lasers comprising:
  1) a semiconductor laser gain medium that, in the absence of a grating filter element, produces laser light having a center frequency within the first frequency range and a first frequency linewidth of at least 1000 GHz;
  2) a grating filter element capable of providing feedback to the light in the laser gain medium, wherein the grating element is adapted to reduce the first frequency linewidth to a second frequency linewidth that is no more than one-half of the first frequency linewidth; and
  3) an output coupling adapted to output a desired fraction of light from the semiconductor laser gain medium as laser pulses;
wherein the diode laser system further comprises:
  4) at least one beam combining optical element; and
  5) at least one collimating optical element,
wherein the at least one beam combining optical element and the at least one collimating optical element combine the output of the plurality of semiconductor lasers into a single laser light output having a common optical axis.

301. A system for treating a target tissue having poor chromophore selectivity, the target tissue comprising a first tissue structure comprising a target chromophore and a second tissue structure comprising a non-target chromophore, wherein the absorption coefficient of the target chromophore continuously exceeds the absorption coefficient of the at least one non-target chromophore over a first frequency range of less than 6000 GHz, and the maximum value of the ratio of the absorption coefficient of the target chromophore to the absorption coefficient of the non-target chromophore over the first frequency range is less than 10, the system comprising:
  a) a diode laser system having at least one semiconductor laser generating pulsed laser light, the at least one semiconductor laser comprising:
    1) a semiconductor laser gain medium that, in the absence of a grating filter element, produces laser light having a center frequency within the first frequency range and a first frequency linewidth of at least 1000 GHz;
    2) a grating filter element capable of providing feedback to the light in the laser gain medium, wherein the grating element is adapted to reduce the first frequency linewidth to a second frequency linewidth that is no more than one-half of the first frequency linewidth; and
    3) an output coupling adapted to output a desired fraction of light from the semiconductor laser gain medium as laser pulses;
  b) a handpiece to receive the laser pulses output from the diode laser system and to direct the laser pulses to the target tissue along a first optical path.

302. The system of claim 301, wherein the handpiece comprises:
  1) an optical connector to receive the laser light output from the output coupling of the diode laser system;
  2) a contact cooling element comprising a cooling window adapted to contact and cool a first skin area of the patient, wherein the cooling window comprises a thermally conductive material and wherein the target tissue comprises a volume of tissue having an external skin surface within the first skin area; and
  3) at least one optical element located in the first optical path and adapted to direct the laser light along the first optical path from the optical connector through the cooling window into the target tissue;
the system further comprising:
  c) a temperature determination unit that determines a surface temperature of the target tissue one or more times before, during, or after the application of each laser pulse.

303. The system of claim 302, wherein the cooling window comprises a thermally conductive material that is transmissive to infrared energy, and the temperature determination unit determines the surface temperature of the target tissue based on infrared energy radiated from the target tissue through the cooling window along a second optical path.

304. The system of claim 303, wherein the handpiece comprises at least one reflective element located in the second optical path, and wherein the temperature determination unit comprises:
  1) a temperature sensing element for sensing infrared energy radiated from substantially only the target tissue through the cooling window along the second optical path, the temperature sensing element generating a first signal indicative of the infrared energy radiating along the second optical path, wherein the infrared energy radiating along the second optical path engages the at least one reflective optical element before being directed onto the temperature sensing element; and
  2) a processor adapted to determine the surface temperature of the target tissue one or more times during or after the application of each therapeutic laser pulse based on the first signal.

305. The method of claim 20, wherein the target chromophore is sebum or sebaceous gland tissue and the non-target chromophore is water.

306. The system of claim 301, wherein the at least one semiconductor laser comprises one of a distributed feedback laser (DFB), a distributed Bragg reflector (DBR) laser, a volume holographic grating (VHG) stabilized laser, and an extended cavity diode laser (ECDL).

The particular embodiments disclosed and discussed above are illustrative only, as the invention may be modified and practiced in different but equivalent manners apparent to those skilled in the art having the benefit of the teachings herein. Embodiments of the present invention disclosed and claimed herein may be made and executed without undue experimentation with the benefit of the present disclosure. While the invention has been described in terms of particular embodiments, it will be apparent to those of skill in the art that variations may be applied to systems and apparatus described herein without departing from the concept and scope of the invention. Examples are all intended to be non-limiting. It is therefore evident that the particular embodiments disclosed above may be altered or modified and all such variations are considered within the scope of the invention, which are limited only by the scope of the claims.

What is claimed is:

1. A method of treating a target tissue having poor chromophore selectivity relative to a non-target tissue, the method comprising: a) selecting for treatment a target tissue comprising a first tissue structure comprising a target chromophore and a second tissue structure comprising at least one non-target chromophore, wherein the absorption coefficient of the target chromophore continuously exceeds the absorption coefficient of the at least one non-target chromophore over a first frequency range of less than 6000 GHz, and the maximum value of the ratio of the absorption coefficient of the target chromophore to the absorption coefficient of the non-target chromophore over the first frequency range is less than 10; b) providing a diode laser system comprising at least one semiconductor laser comprising: 1) a semiconductor laser gain medium that, in the absence of a grating filter element, is adapted to produce laser light having a center frequency within the first frequency range and a first frequency linewidth of at least 1000 GHz; 2) a grating filter element capable of providing feedback to the light in the laser gain medium, wherein the grating element is further capable of reducing the first frequency linewidth to a second frequency linewidth that is no more than one-half of the first frequency linewidth; and 3) an output coupling adapted to output a predetermined fraction of light from the semiconductor laser gain medium; c) generating laser light in a resonant cavity of the diode laser system; d) filtering the generated laser light using the grating filter element; e) outputting from the output coupling, a laser light having the center frequency and the second frequency linewidth of no more than 500 GHz; and f) applying the laser light output from the output coupling to the target tissue for selectively heating the target chromophore relative to the non-target chromophore.

2. The method of claim 1, wherein outputting laser light from the output coupler comprises outputting laser light having the center frequency and the second frequency linewidth of no more than 300 GHz.

3. The method of claim 1, wherein outputting laser light from the output coupler comprises outputting pulsed laser light having the center frequency and the second frequency linewidth of no more than 200 GHz.

4. The method of claim 1, wherein the grating filter element is adapted to reduce the first frequency linewidth by at least 75%.

5. The method of claim 1, wherein outputting from the output coupling comprises outputting laser light for which at least 50% of energy of the output laser light is at a frequency for which the ratio of the absorption coefficient of the first chromophore to the absorption coefficient of the second chromophore is at least 75% of the maximum value of the absorption coefficient ratio over the first frequency range.

6. The method of claim 5, wherein outputting from the output coupling comprises outputting light for which at least 75% of the energy of the output laser light is at a frequency for which the ratio of the absorption coefficient of the first chromophore to the absorption coefficient of the second chromophore is at least 90% of the maximum value of the absorption coefficient ratio over the first frequency range.

7. The method of claim 6, wherein outputting from the output coupling comprises outputting light for which at least 100% of the energy of the output laser light is at a frequency for which the ratio of the absorption coefficient of the first chromophore to the absorption coefficient of the second chromophore is at least 90% of the maximum value of the absorption coefficient ratio over the first frequency range.

8. The method of claim 1, further comprising:
g) providing a cooling system for the at least one semiconductor laser, the cooling system comprising a heat sink at a desired temperature to cool the at least one semiconductor laser; and
h) operating the cooling system for the at least one semiconductor laser to maintain the at least one semiconductor laser at a temperature that varies by no more than 40° C. during steps of c) generating the laser light and f) applying the laser light to the target tissue.

9. The method of claim 8, wherein providing the cooling system comprises providing the heat sink and controlling the temperature of the heat sink to a desired temperature within the range of 10-40° C.

10. The method of claim 9, wherein providing the cooling system comprises providing the heat sink and controlling the temperature of the heat sink to a desired temperature within the range of 20-35° C.

11. The method of claim 9, wherein providing the heat sink at a desired temperature comprises providing a heat sink and maintaining the heat sink at a temperature that varies by no more than 5° C. during the steps of c) generating laser light and D applying the laser light to the target tissue.

12. The method of claim 8, wherein operating the cooling system for the at least one semiconductor laser allows the grating filter element to reduce the first frequency linewidth during the step of outputting laser light to no more than 500 MHz.

13. The method of claim 12, wherein operating the cooling system for the at least one semiconductor laser allows the grating filter element to reduce the first frequency linewidth during the step of outputting laser light to no more than 300 MHz.

14. The method of claim 8, wherein providing the cooling system comprises: 1) providing the heat sink having a thermally conductive baseplate; and 2) maintaining the thermally conductive baseplate at a constant temperature within the range of 20-35° C.

15. The method of claim 1, wherein providing a diode laser system comprises providing a plurality of semiconductor lasers, each laser of the plurality of semiconductor lasers comprising:
1) a semiconductor laser gain medium that, in the absence of a grating filter element, produces laser light having a center frequency within the first frequency range and a first frequency linewidth of at least 1000 GHz;

2) a grating filter element capable of providing feedback to the light in the laser gain medium, wherein the grating element is further capable of reducing the first frequency linewidth by at least one-half; and 3) an output coupling adapted to output a desired fraction of light from the semiconductor laser gain medium;

wherein providing a diode laser system further comprises:

4) providing at least one beam combining optical element, and;

5) providing at least one collimating optical element, wherein the at least one beam combining optical element and the at least one collimating optical element combine the output of the plurality of semiconductor lasers into a single laser light output having a common optical axis.

16. The method of claim 1, further comprising: g) providing a handpiece comprising: 1) an optical connector to receive the laser light output from the output coupling of the diode laser system and to direct the laser light to the target tissue along a first optical path; 2) a first optical element comprising a reflective element and having a first open portion comprising one of an aperture and a slot; 3) at least a second optical element comprising at least one of a refractive element and a second reflective element; 4) a contact cooling element comprising a cooling window adapted to contact and cool a first skin area comprising a target skin area comprising the target tissue, wherein the cooling window comprises a thermally conductive material that is transmissive to infrared energy and to the laser light; and 5) a temperature determination unit for determining a surface temperature of the target tissue based on infrared energy radiated from the target tissue through the cooling window along a second optical path; wherein applying the laser light to the target tissue comprises: 1) receiving the laser light from the diode laser system using the optical connector; and 2) directing the laser light along the first optical path by engaging the at least a second optical element and passing through the cooling window to the target tissue.

17. The method of clam 1, wherein the target chromophore is sebum or sebaceous gland tissue and the non-target chromophore is water.

18. The method of claim 1, wherein providing a diode laser system comprises providing at least one of a distributed feedback (DFB) laser, a distributed Bragg reflector (DBR) laser, a volume holographic grating (VHG) stabilized laser, and an extended cavity diode laser (ECDL).

19. The method of claim 1, wherein selecting for treatment a target tissue comprises selecting a target tissue for which the maximum value of the ratio of the absorption coefficient of the target chromophore to the absorption coefficient of the non-target chromophore over the first frequency range is less than 5.

20. A method of selectively treating sebum in a target tissue comprising sebum and water as chromophores, comprising: a) selecting a skin area comprising a sebaceous gland as a target chromophore and water as a non-target chromophore for treatment with one or more therapeutic laser pulses with laser light having a wavelength within a first frequency range of about 1690-1740 nm, wherein the maximum value of the ratio of the absorption coefficient of sebum to the absorption coefficient of water over the first frequency range is less than 5; b) providing a diode laser system comprising at least one semiconductor laser comprising: 1) a semiconductor laser gain medium that, in the absence of a grating filter element, is adapted to produce laser light having a center frequency within the first frequency range and a first frequency linewidth of at least 1000 GHz; 2) a grating filter element capable of providing feedback to the laser light produced in the laser gain medium, wherein the grating element is further capable of reducing the first frequency linewidth to a second frequency linewidth that is no more than one-half of the first frequency linewidth; and 3) an output coupling adapted to output a predetermined fraction of light from the semiconductor laser gain medium; c) generating laser light in a resonant cavity of the diode laser system; d) filtering the generated laser light using the grating filter element; e) outputting from the output coupling, a laser light having the center frequency and the second frequency linewidth of no more than 300 GHz; and f) applying the laser light output from the output coupling to the target tissue for selectively heating the sebum relative to water in the target tissue.

21. The method of claim 20, wherein outputting from the output coupling comprises outputting laser light for which at least 50% of the energy of the output laser light is at a frequency for which the ratio of the absorption coefficient of the first chromophore to the absorption coefficient of the second chromophore is at least 75% of the maximum value of the absorption coefficient ratio over the first frequency range.

22. The method of claim 20, wherein outputting from the output coupling comprises outputting light for which at least 75% of energy of the output laser light is at a frequency for which the ratio of the absorption coefficient of the first chromophore to the absorption coefficient of the second chromophore is at least 90% of the maximum value of the absorption coefficient ratio over the first frequency range.

23. The method of claim 20, wherein outputting from the output coupling comprises outputting light for which at least 100% of energy of the output laser light is at a frequency for which the ratio of the absorption coefficient of the first chromophore to the absorption coefficient of the second chromophore is at least 90% of the maximum value of the absorption coefficient ratio over the first frequency range.

24. The method of claim 20, wherein outputting from the output coupling comprises outputting light for 100% of energy of the output laser light is at a frequency within the range of 1725-1728 nm.

25. The method of claim 20, further comprising:

g) providing a cooling system for the at least one semiconductor laser, the cooling system comprising a heat sink at a desired temperature to cool the at least one semiconductor laser; and h) operating the cooling system for the at least one semiconductor laser to maintain the at least one semiconductor laser at a temperature that varies by no more than 40° C. during steps of c) generating the laser light and f) applying the laser light to the target tissue.

26. The method of claim 25, wherein providing the cooling system comprises providing the heat sink and controlling the temperature of the heat sink to a desired temperature within a range of 10-40° C.

27. The method of claim 26, wherein providing the cooling system comprises providing the heat sink and controlling the temperature of the heat sink to a desired temperature within a range of 20-35° C.

28. The method of claim 26, wherein providing a heat sink at a desired temperature comprises providing the heat sink and maintaining the heat sink at a temperature that varies by no more than 5° C. during the steps of c) generating laser light and D applying the laser light to the target tissue.

29. The method of claim 25, wherein providing a cooling system comprises: 1) providing the heat sink having a thermally conductive baseplate; and 2) maintaining the thermally conductive baseplate at a constant temperature within a range of 20-35° C.

* * * * *